US011331277B2

(12) United States Patent
Gu et al.

(10) Patent No.: US 11,331,277 B2
(45) Date of Patent: May 17, 2022

(54) H₂O₂-RESPONSIVE NANOPARTICLES AND USES THEREOF

(71) Applicant: NORTH CAROLINA STATE UNIVERSITY, Raleigh, NC (US)

(72) Inventors: Zhen Gu, Raleigh, NC (US); Xiuli Hu, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 327 days.

(21) Appl. No.: 16/466,695

(22) PCT Filed: Dec. 5, 2017

(86) PCT No.: PCT/US2017/064725
§ 371 (c)(1),
(2) Date: Jun. 5, 2019

(87) PCT Pub. No.: WO2018/106697
PCT Pub. Date: Jun. 14, 2018

(65) Prior Publication Data
US 2019/0298659 A1 Oct. 3, 2019

Related U.S. Application Data

(60) Provisional application No. 62/430,273, filed on Dec. 5, 2016.

(51) Int. Cl.
| | |
|---|---|
| A61K 9/51 | (2006.01) |
| A61K 9/00 | (2006.01) |
| A61K 9/107 | (2006.01) |
| A61K 38/28 | (2006.01) |
| A61K 47/34 | (2017.01) |
| A61K 47/36 | (2006.01) |
| A61P 3/10 | (2006.01) |
| B82Y 5/00 | (2011.01) |
| A61M 37/00 | (2006.01) |

(52) U.S. Cl.
CPC .......... *A61K 9/5146* (2013.01); *A61K 9/0021* (2013.01); *A61K 9/1075* (2013.01); *A61K 38/28* (2013.01); *A61K 47/34* (2013.01); *A61K 47/36* (2013.01); *A61M 37/00* (2013.01); *A61P 3/10* (2018.01); *B82Y 5/00* (2013.01)

(58) Field of Classification Search
CPC ...... A61K 9/0021; A61K 38/28; A61K 47/34; A61K 47/36; A61K 9/1075; A61K 9/5146; A61M 37/00; A61P 3/10; B82Y 5/00
See application file for complete search history.

(56) References Cited

U.S. PATENT DOCUMENTS

2008/0312610 A1* 12/2008 Binks ............... A61P 29/00
604/272

FOREIGN PATENT DOCUMENTS

WO 20160172320 10/2016

OTHER PUBLICATIONS

DiSanto et al.; "Recent Advances in Nanotechnology for Diabetes Treatment"; Wiley Interdiscip Rev Nanomed Nanobiotechnol. Published in final edited form: Jul. 2015; 7(4): 548-564. Published online: Jan. 15, 2015.*
Wang et al.; "Leveraging H2O2 Levels for Biomedical Applications"; Adv. Biosys. 2017, 1, 1700084; 15 pages; published Jul. 17, 2017.*
Anraku, Yasutaka, et al. "Systemically Injectable Enzyme-Loaded Polyion Complex Vesicles as In Vivo Nanoreactors Functioning in Tumors." Angewandte Chemie International Edition 55.2 (2016): 560-565.
Bariya, Shital H., et al. "Microneedles: an emerging transdermal drug delivery system." Journal of Pharmacy and Pharmacology 64.1 (2012): 11-29.
Bratlie, Kaitlin M., et al. "Materials for diabetes therapeutics." Advanced healthcare materials 1.3 (2012): 267-284.
Broaders, Kyle E., Sirisha Grandhe, and Jean MJ Fréchet. "A biocompatible oxidation-triggered carrier polymer with potential in therapeutics." Journal of the American Chemical Society 133.4 (2011): 756-758.
Brownlee, M.; Cerami, A. A Glucose-Controlled Insulin-Delivery System: Semisynthetic Insulin Bound to Lecitin. Science 1979, 206, 1190-1191.
Chou, Danny Hung-Chieh, et al. "Glucose-responsive insulin activity by covalent modification with aliphatic phenylboronic acid conjugates." Proceedings of the National Academy of Sciences 112.8 (2015): 2401-2406.
Choudhary, Pratik, et al. "Insulin pump therapy with automated insulin suspension in response to hypoglycemia: reduction in nocturnal hypoglycemia in those at greatest risk." Diabetes care 34.9 (2011): 2023-2025.

(Continued)

*Primary Examiner* — Jeffrey T. Palenik
(74) *Attorney, Agent, or Firm* — Meunier Carlin & Curfman LLC

(57) ABSTRACT

Disclosed herein is a nanoparticle comprising a copolymer comprising a polyethylene glycol polymer, a polyhydroxylated polymer, and a peroxide-sensitive pendant group; a glucose-responsive agent; and a therapeutic agent; wherein the copolymer encapsulates the glucose-responsive agent and the therapeutic agent. Also disclosed herein is a method of delivering a therapeutic agent to a subject comprising administering to the subject a nanoparticle comprising a copolymer comprising a polyethylene glycol polymer, a polyhydroxylated polymer, and a peroxide-sensitive pendant group; a glucose-responsive agent; and a therapeutic agent; wherein the copolymer encapsulates the glucose-responsive agent and the therapeutic agent; and releasing the therapeutic agent from the nanoparticle in the presence of hyperglycemic levels of glucose. In some embodiments, the glucose-responsive agent produces a peroxide when exposed to hyperglycemic levels of glucose, thereby triggering disassembly of the nanoparticle and release of encapsulated therapeutic agent.

18 Claims, 14 Drawing Sheets

(56) References Cited

OTHER PUBLICATIONS

De Gracia Lux, Caroline, et al. "Biocompatible polymeric nanoparticles degrade and release cargo in response to biologically relevant levels of hydrogen peroxide." Journal of the American Chemical Society 134.38 (2012): 15758-15764.
Discher, Dennis E., and Adi Eisenberg. "Polymer vesicles." Science 297.5583 (2002): 967-973.
Donnelly, Ryan F., Thakur Raghu Raj Singh, and A. David Woolfson. "Microneedle-based drug delivery systems: microfabrication, drug delivery, and safety." Drug delivery 17.4 (2010): 187-207.
Elsabahy, Mahmoud, et al. "Polymeric nanostructures for imaging and therapy." Chemical reviews 115.19 (2015): 10967-11011.
Gaitzsch, Jens, et al. "Synthetic bio-nanoreactor: mechanical and chemical control of polymersome membrane permeability." Angewandte Chemie International Edition 51.18 (2012): 4448-4451.
Gittard, Shaun D., et al. "The effects of geometry on skin penetration and failure of polymer microneedles." Journal of adhesion science and technology 27.3 (2013) 227-243.
Gordijo, Claudia R., Adam J. Shuhendler, and Xiao Yu Wu. "Glucose-responsive bioinorganic nanohybrid membrane for self-regulated insulin release." Advanced Functional Materials 20.9 (2010): 1404-1412.
Gu, Zhen, et al. "Glucose-responsive microgels integrated with enzyme nanocapsules for closed-loop insulin delivery." ACS nano 7.8 (2013): 6758-6766.
Jeandidier, Nathalie, and Sophie Boivin. "Current status and future prospects of parenteral insulin regimens, strategies and delivery systems for diabetes treatment." Advanced drug delivery reviews 35.2-3 (1999): 179-198.
Joshi-Barr, Shivanjali, et al. "Exploiting oxidative microenvironments in the body as triggers for drug delivery systems." Antioxidants & redox signaling 21.5 (2014): 730-754.
Kim, Hyunkyu, et al. "Monosaccharide-responsive release of insulin from polymersomes of polyboroxole block copolymers at neutral pH." Journal of the American Chemical Society 134.9 (2012): 4030-4033.
Kim, Sung Wan, et al. "Self-regulated glycosylated insulin delivery." Journal of controlled release 11.1-3 (1990): 193-201.
Kim, Yeu-Chun, Jung-Hwan Park, and Mark R. Prausnitz. "Microneedles for drug and vaccine delivery." Advanced drug delivery reviews 64.14 (2012): 1547-1568.
Kitano, Shigeru, et al. "A novel drug delivery system utilizing a glucose responsive polymer complex between poly (vinyl alcohol) and poly (N-vinyl-2-pyrrolidone) with a phenylboronic acid moiety." Journal of controlled release 19.1-3 (1992): 161-170.
Lee, Sue Hyun, et al. "Current progress in reactive oxygen species (ROS)—responsive materials for biomedical applications." Advanced healthcare materials 2.6 (2013): 908-915.
Li, Yamin, et al. "Enzyme-responsive polymeric vesicles for bacterial-strain-selective delivery of antimicrobial agents." Angewandte Chemie International Edition 55.5 (2016): 1760-1764.
Liu, Xin, et al. "Fusogenic reactive oxygen species triggered charge-reversal vector for effective gene delivery." Advanced Materials 28.9 (2016): 1743-1752.
Lu, Hua, et al. "Ionic polypeptides with unusual helical stability." Nature communications 2.1 (2011): 1-9.
Lu, Y.; Aimetti, A. A.; Langer, R.; Gu, Z. Bioresponsive Materials. Nat. Rev. Mater. 2016, 1, 16075.
Ma, Rujiang, and Linqi Shi. "Phenylboronic acid-based glucose-responsive polymeric nanoparticles: synthesis and applications in drug delivery." Polymer Chemistry 5.5 (2014): 1503-1518.
Mahmoud, Enas A., et al. "Inflammation responsive logic gate nanoparticles for the delivery of proteins." Bioconjugate chemistry 22.7 (2011): 1416-1421.
Mai, Yiyong, and Adi Eisenberg. "Self-assembly of block copolymers." Chemical Society Reviews 41.18 (2012): 5969-5985.
Martino, Chiara, et al. "Protein expression, aggregation, and triggered release from polymersomes as artificial cell-like structures." Angewandte Chemie International Edition 51.26 (2012): 6416-6420.
Matsumoto, Akira, et al. "A synthetic approach toward a self-regulated insulin delivery system." Angewandte Chemie International Edition 51.9 (2012): 2124-2128.
Mo, Ran, et al. "Emerging micro-and nanotechnology based synthetic approaches for insulin delivery." Chemical society reviews 43.10 (2014): 3595-3629.
Napoli, Alessandro, et al. "Glucose-oxidase based self-destructing polymeric vesicles." Langmuir 20.9 (2004): 3487-3491.
Napoli, Alessandro, et al. "Oxidation-responsive polymeric vesicles." Nature materials 3.3 (2004): 183-189.
Palivan, Cornelia G., et al. "Bioinspired polymer vesicles and membranes for biological and medical applications." Chemical society reviews 45.2 (2016): 377-411.
Podual, Kairali, Francis J. Doyle III, and Nicholas A. Peppas. "Glucose-sensitivity of glucose oxidase-containing cationic copolymer hydrogels having poly (ethylene glycol) grafts." Journal of Controlled Release 67.1 (2000): 9-17.
Podual, K., F. J. Doyle Iii, and N. A. Peppas. "Preparation and dynamic response of cationic copolymer hydrogels containing glucose oxidase." Polymer 41.11 (2000): 3975-3983.
Prausnitz, Mark R. "Microneedles for transdermal drug delivery." Advanced drug delivery reviews 56.5 (2004): 581-587.
Raskin, Philip, et al. "Initiating insulin therapy in type 2 diabetes: a comparison of biphasic and basal insulin analogs." Diabetes care 28.2 (2005): 260-265.
Russell, Steven J., et al. "Outpatient glycemic control with a bionic pancreas in type 1 diabetes." New England Journal of Medicine 371.4 (2014): 313-325.
Saravanakumar, Gurusamy, Jihoon Kim, and Won Jong Kim. "Reactive-oxygen-species-responsive drug delivery systems: promises and challenges." Advanced Science 4.1 (2017): 1600124.
Shaw, Jonathan E., Richard A. Sicree, and Paul Z. Zimmet. "Global estimates of the prevalence of diabetes for 2010 and 2030." Diabetes research and clinical practice 87.1 (2010): 4-14.
Städler, Brigitte, Andrew D. Price, and Alexander N. Zelikin. "A critical look at multilayered polymer capsules in biomedicine: drug carriers, artificial organelles, and cell mimics." Advanced Functional Materials 21.1 (2011): 14-28.
Stevenson, Cynthia L., John T. Santini Jr, and Robert Langer. "Reservoir-based drug delivery systems utilizing micro technology." Advanced drug delivery Yeviews 64.14 (2012): 1590-1602.
Stumvoll, Michael, Barry J. Goldstein, and Timon W. Van Haeften. "Type 2 diabetes: principles of pathogenesis and therapy." The Lancet 365.9467 (2005): 1333-1346.
Sullivan, Sean P., et al. "Dissolving polymer microneedle patches for influenza vaccination." Nature medicine 16.8 (2010): 915.
Tai, Wanyi, et al. "Bio-inspired synthetic nanovesicles for glucose-responsive release of insulin." Biomacromolecules 15.10 (2014): 3495-3502.
Tanner, Pascal, et al. "Polymeric vesicles: from drug carriers to nanoreactors and artificial organelles." Accounts of chemical research 44.10 (2011): 1039-1049.
Thabit, H.; Hovorka, R.; Evans, M. "Artificial pancreas: the bridge to a cure for type 1 diabetes." Eur. Diabetes Nur. 2012, 9, 56-60.
Tu, Yingfeng, et al. "Mimicking the cell: bio-inspired functions of supramolecular assemblies." Chemical reviews 116.4 (2016): 2023-2078.
Van Dongen, Stijn FM, et al. "A three-enzyme cascade reaction through positional assembly of enzymes in a polymersome nanoreactor." Chemistry—A European Journal 15.5 (2009): 1107-1114.
Van Dongen, Stijn FM, et al. "Cellular Integration of an Enzyme-Loaded Polymersome Nanoreactor." Angewandte Chemie International Edition 49.40 (2010): 7213-7216.
Veiseh, Omid, et al. "Managing diabetes with nanomedicine: challenges and opportunities." Nature Reviews Drug Discovery 14.1 (2015): 45-57.
Wang, Chao, et al. "Enhanced cancer immunotherapy by microneedle patch-assisted delivery of anti-PD1 antibody." Nano letters 16.4 (2016): 2334-2340.
Wang, Jing, et al. "Supramolecular polymerization from polypeptide-grafted comb polymers." Journal of the American Chemical Society 133.33 (2011): 12906-12909.

(56) References Cited

OTHER PUBLICATIONS

Wang, Ming, et al. "Combinatorially designed lipid-like nanoparticles for intracellular delivery of cytotoxic protein for cancer therapy." Angewandte Chemie International Edition 53.11 (2014): 2893-2898.

Wild, Sarah, et al. "Global prevalence of diabetes: estimates for the year 2000 and projections for 2030." Diabetes care 27.5 (2004): 1047-1053.

Wilson, D. Scott, et al. "Orally delivered thioketal nanoparticles loaded with TNF-α-siRNA target inflammation and inhibit gene expression in the intestines." Nature materials 9.11 (2010): 923-928.

Wu, Qian, et al. "Organization of glucose-responsive systems and their properties." Chemical reviews 111.12 (2011): 7855-7875.

Yang, Sixing, et al. "Phase-transition microneedle patches for efficient and accurate transdermal delivery of insulin." Advanced Functional Materials 25.29 (2015): 4633-4641.

Yu, Jicheng, et al. "Microneedle-array patches loaded with hypoxia-sensitive vesicles provide fast glucose-responsive insulin delivery." Proceedings of the National Academy of Sciences 112.27 (2015): 8260-8265.

International Preliminary Report on Patentability issued for Application No. PCT/US2017/064725, dated Jun. 20, 2019.

International Search Report in PCT/US2017/064725, dated Mar. 22, 2018. 9 pages.

Wanyi Tai et al. Bio-Inspired Synthetic Nanovesicles for Glucose Responsive Release of Insulin. Biomacromolecules, 2014, vol. 15, pp. 3495-3502, especially p. 3496, col. I, lines 15-22, figs. 1, 5A, 7B.

Rujiang Ma et al. Phenylboronic Acid-Based Complex Micelles with Enhanced Glucose-Responsiveness at Physiological pH by Complexation with Glycopolymer. Biomacromolecules, 2012, vol. 13, pp. 3409-3417, especially abstract, scheme I, p. 3409, col. 2, lines 4-8, p. 3410, col. 2, lines 1-5.

\* cited by examiner

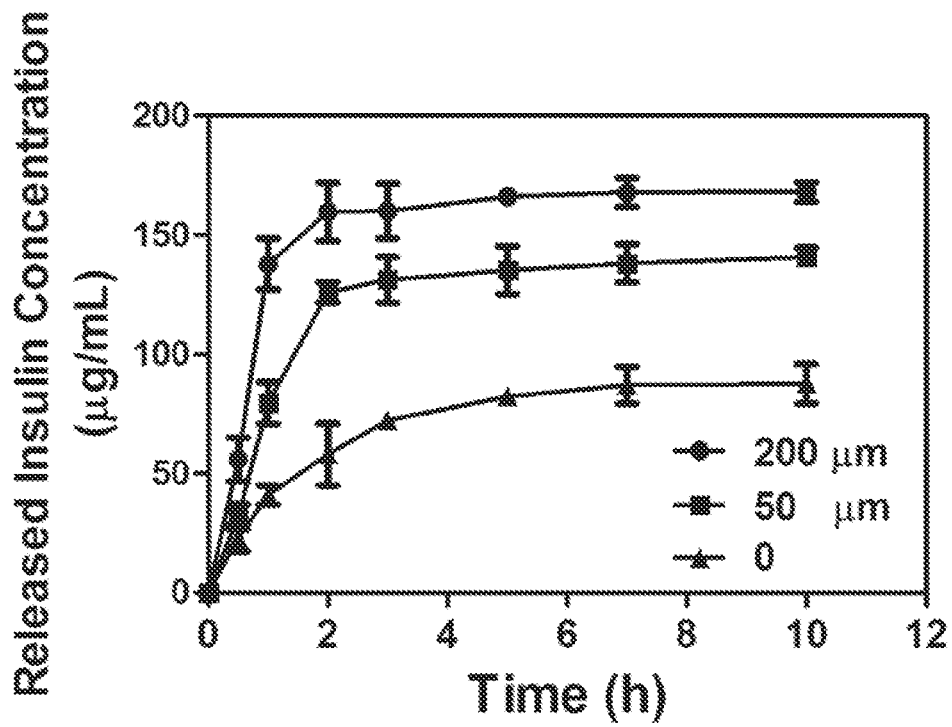
FIG. 6
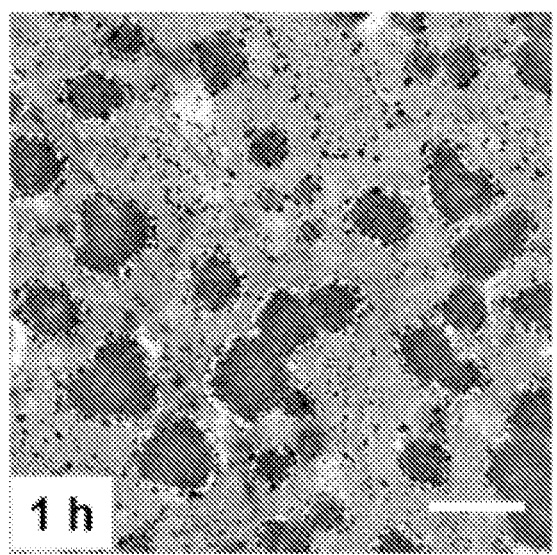 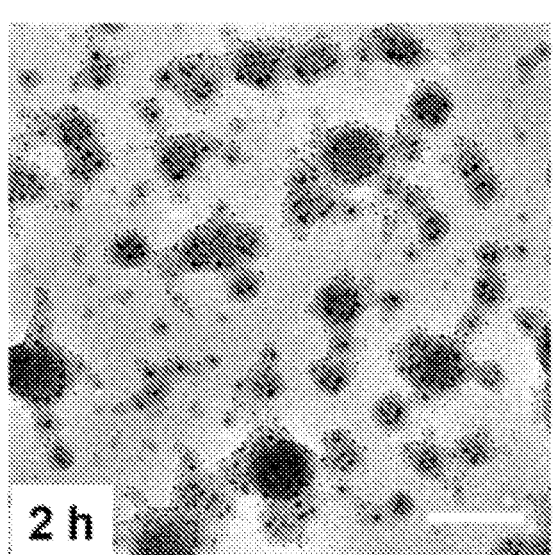
FIG. 7A					FIG. 7B

H₂O₂-RESPONSIVE NANOPARTICLES AND USES THEREOF

CROSS REFERENCE TO RELATED APPLICATIONS

This application claims the benefit of U.S. Provisional Patent Application Serial No. 62/430,273, filed Dec. 5, 2016, the disclosure of which is expressly incorporated herein by reference.

STATEMENT REGARDING FEDERALLY SPONSORED RESEARCH OR DEVELOPMENT

This invention was made with Government Support under Grant No. 1160483 awarded by the National Science Foundation. The Government has certain rights in the invention.

BACKGROUND

Diabetes mellitus is a chronic metabolic disorder characterized by elevated blood glucose levels. It has become one of the most challenging global health issues and the number of people living with diabetes has increased dramatically. Traditional care for type 1 and advanced type 2 diabetic patients requires frequent or constant monitoring of glycemic levels combined with frequent subcutaneous injections of long- and short-acting insulin or using continuous and variable insulin infusions towards the goal of maintaining normoglycemia. Nevertheless, such "open-loop" self-administration of insulin is always painful and generally associated with inadequate glucose control.

An alternative to these traditional, open-loop methods of insulin delivery is the use of a closed-loop insulin pump integrated with a continuous glucose monitor. This closed-loop principle can increase efficiency in blood glucose control and reduce the risk of hypoglycemia. See Choudhary, et al., *Diabetes Care*, 2011, 34:2023; see also Russell, et al., *Engl. J. Med.* 2014, 371:313. However, there are still several obstacles to overcome regarding the accuracy of the continuous glucose monitor and reliability of insulin infusions. See Bratlie, et al., *Adv. Drug Delivery Rev.*, 2012, 1:267; see also Stevenson, et al., *Adv. Drug Delivery Rev.* 2012, 64:1590. Further, the current systems require tubing and subcutaneous implantation of a cannula, which is inconvenient and often associates with biofouling.

Meanwhile, synthetic glucose-responsive materials have been explored for achieving closed-loop insulin release, offering the potential of insulin delivery without these limitations. See Wu, et al., *Chem. Rev.*, 2011, 111:7855. The matrix typically employs glucose-responsive moieties such as glucose oxidase (GOx), phenylboronic acid (PBA), or glucose binding proteins (GBP) to regulate the release rate of the pre-loaded insulin by polymer degradation, structure switch or glucose binding competition. See Gu, et al., *ACS Nano* 2013, 7:6758; Ma, et al., *Polym. Chem.*, 2014, 5:1503; Brownlee, et al., *Science*, 1979, 206:1190. However, there remains a challenge to demonstrate a desirable system, which combines (i) ease of use, (ii) high drug loading capacity, (iii) fast responsiveness, and (iv) excellent biocompatibility. For example, most glucose-responsive formulations that incorporate GOx involve pH-sensitive materials, based on the enzymatic oxidation of glucose to gluconic acid. These systems are limited because of the challenge to rapidly switch the physiological pH in vivo. See Mo, et al., *Chem. Soc. Rev.*, 2014, 43:3595. A hypoxia-sensitive formulation was developed to achieve faster response. See Yu, et al., *Proc. Natl. Acad. Sci.*, 2015, 112:8260. However, hydrogen peroxide ($H_2O_2$) remains in this hypoxia-sensitive system, which causes long-term biocompatibility concerns. See Saravanakumar, et al., *Adv. Sci.*, 2016, 4(1): 1600124.

SUMMARY

Disclosed herein are nanoparticle compositions comprising therapeutic agents and methods for delivering therapeutic agents.

In one aspect, disclosed herein is a nanoparticle comprising: a copolymer comprising a polyethylene glycol polymer, a polyhydroxylated polymer, and a peroxide-sensitive pendant group; a glucose-responsive agent; and a therapeutic agent; wherein the copolymer encapsulates the glucose-responsive agent and the therapeutic agent. In some embodiments, the polyhydroxylated polymer comprises polyserine. In some embodiments, the glucose-responsive agent comprises glucose oxidase. In some embodiments, the therapeutic agent comprises insulin.

In another aspect, disclosed herein is a method of delivering a therapeutic agent to a subject comprising administering to the subject a nanoparticle comprising a copolymer comprising a polyethylene glycol polymer, a polyhydroxylated polymer, and a peroxide-sensitive pendant group; a glucose-responsive agent; and a therapeutic agent; wherein the copolymer encapsulates the glucose-responsive agent and the therapeutic agent; and releasing the therapeutic agent from the nanoparticle in the presence of hyperglycemic levels of glucose. In some embodiments, the glucose-responsive agent produces a peroxide when exposed to hyperglycemic levels of glucose. In some embodiments, the method further comprises detaching the peroxide-sensitive pendant group from the polyhydroxylated polymer upon exposure to the peroxide. In some embodiments, the detaching step increases solubility of the copolymer in water. In some embodiments, the increased water solubility of the copolymer dissociates the copolymer from the therapeutic agent, thereby releasing the therapeutic agent from the nanoparticle.

The details of one or more embodiments of the invention are set forth in the accompanying drawings and the description below. Other features, objects, and advantages of the invention will be apparent from the description and drawings, and from the claims.

DESCRIPTION OF DRAWINGS

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are for purposes of example and explanation only and are not restrictive of the disclosure.

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

FIG. 1A shows conceptual construction of nanoparticles by self-assembly of the block copolymer mPEG-b-P(Ser-PBE) into nanoparticles loaded with insulin and GOx. The nanoparticles dissociate in the presence of hyperglycemic levels of glucose, triggered by increased $H_2O_2$ levels, thereby releasing insulin. FIG. 1B shows conceptual construction of a hyaluronic acid (HA)-based microneedle-array patch loaded with nanoparticles administrable to skin for smart insulin delivery in a mouse model of type 1 diabetes.

FIG. 2A shows the construction and chemical structure of 4-(Hydroxymethyl)phenylboronic acid pinacol ester (PBE; compound 1), which was then used to construct pendant groups on polyserine, thereby forming mPEG-b-P (Ser-PBE). Peroxide-mediated degradation products of mPEG-b-P(Ser-PBE) are also shown. FIG. 2B is a graph showing 1H NMR spectra of mPEG-b-P(Ser-PBE).

FIG. 3A is a TEM image of blank polymeric nanoparticles (PVs). FIG. 3B is a TEM image of PVs encapsulated with GOx enzyme and insulin (PVs(E+I)). In FIGS. 3A-B, the scale bar represents 200 nm. FIG. 3C is a graph depicting diameter distributions of empty PVs and slightly larger PV(E+I) determined by dynamic light scatting (DLS).

FIG. 6 is a graph depicting in vitro release of insulin from PVs(E+I) at different $H_2O_2$ concentrations at 37° C.

FIGS. 7A-C depict size characterization of PVs over time upon exposure to a hyperglycemic level (400 mg/dL) of glucose. Changes in PV morphology are shown in TEM image of PV(E+I) post-incubation in glucose solution for 1 hour (FIG. 7A) and 2 hours (FIG. 7B) at 37° C. In FIGS. 7A-B, the scale bar represents 200 nm. FIG. 7C is a graph depicting diameter distributions of PV(E+I) incubated in glucose solution for varying times, as determined by dynamic light scatting (DLS).

FIG. 8A shows concentrations of released insulin from PVs(E+I) at several glucose concentrations over time at 37° C. FIG. 8B shows the release rate (line slope) of insulin as a function of glucose concentration in the media for PV(E+I) and PV(1/2E+I) (containing one half the amount of GOx enzyme compared to PV(E+I)). FIG. 8C shows the pulsatile insulin release profile of PV(E+I) when the glucose concentration was repeatedly changed between 100 and 400 mg/dL every 10 min. FIG. 8D shows a circular dichroism (CD) spectra of native, non-encapsulated insulin and insulin released from PVs incubated with 400 mg/mL glucose. Error bars indicate SD (n=3).

FIG. 9A shows a fluorescence microscopy image of MNs loaded with PVs containing FITC-labelled insulin. (Inset is zoomed-in image of MN). Scale bar represents 200 μm. FIG. 9B shows trypan blue staining of mouse skin transcutaneously treated with an MN-array patch for 1 hour. FIG. 9C shows a H&E-stained section of mouse skin penetrated by MN-array patch. The skin muscle and fat tissue regions are indicated by M and F, respectively. The region where MN patch insertion took place is indicated by the black dashed line.

FIG. 11A shows blood glucose levels in STZ-induced diabetic mice after treatment with hyaluronic acid-containing MN patches alone (MN[HA]), MN patches loaded with insulin (MN[I]), MN patches loaded with vesicles encapsulating GOx enzyme and insulin (MN[PV (E+I)]), and MN patches loaded with vesicles encapsulating insulin alone (MN[PV(I)]). *P<0.05 for administration with MN[PV(E+I)] compared with MN[I]. FIG. 11B shows human insulin concentrations in plasma of STZ-induced diabetic mice after treatment with MN[PV(E+I)] and MN[PV(I)]. *P<0.05 for administration with MN[PV(E+I)] compared with MN[PV(I)].

FIG. 12A shows results of an in vivo glucose tolerance test in diabetic mice 1 hour post-administration of MN[PV(E+I)] or MN[I] in comparison to the healthy mice. *P<0.05 for administration with MN[PV(E+I)] compared with MN[I]. FIG. 12B shows responsiveness of patch-treated and glucose-challenged diabetic mice, as measured by blood glucose levels. The area under the curve (AUV) up to 150 min shown in FIG. 12A was calculated, with the baseline set at the 0-min blood glucose reading. *P<0.05 for administration with MN[I] compared with healthy mice.

FIG. 13A shows blood glucose changes of healthy (non-diabetic) mice treated with MN patches over time. *P<0.05 for administration with MN[PV(E+I)] compared with MN[I]. FIG. 13B shows quantification of the hypoglycemia index, which was calculated as the difference between the initial and nadir blood glucose readings divided by the time at which the nadir was reached. *P<0.05 for administration with MN[PV(E+I)] compared with MN[PV(I)]. Error bars indicate SD (n=5).

DETAILED DESCRIPTION

Figure 1A:
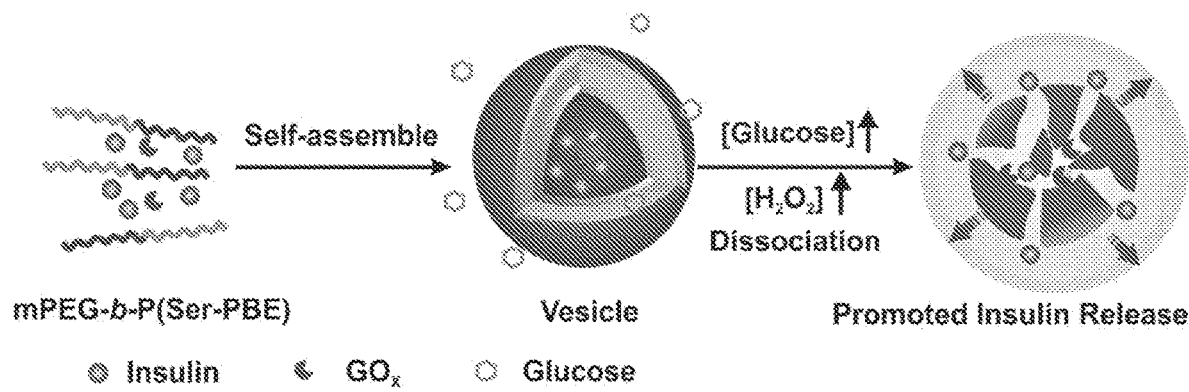
FIGS. 1A-B are schematics depicting $H_2O_2$-responsive nanoparticles for glucose-triggered insulin delivery.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this disclosure belongs. The term "comprising" and variations thereof as used herein is used synonymously with the terms "including," "containing," and variations thereof and are open, non-limiting terms. Although the terms "comprising," "including," and "containing" have been used herein to describe various embodiments, the terms "consisting essentially of" and "consisting of" can be used in place of "comprising," "including," and "containing" to provide for more specific embodiments and are also disclosed.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular nanoparticle is disclosed and discussed and a number of modifications that can be made to the nanoparticle are discussed, specifically contemplated is each and every combination and permutation of the nanoparticle and the modifications that are possible unless specifically indicated to the contrary. Thus, if a class of nanoparticles A, B, and C are disclosed as well as a class of nanoparticles D, E, and F and an example of a combination nanoparticle, or, for example, a combination nanoparticle comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In some non-limiting embodiments, the terms are defined to be within 10% of the associated value provided. In some non-limiting embodiments, the terms are defined to be within 5%. In still other non-limiting embodiments, the terms are defined to be within 1%.

"Administration" to a subject includes any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Biocompatible" generally refers to a material and any metabolites or degradation products thereof that are generally non-toxic to the recipient and do not cause significant adverse effects to the subject.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention. It is expressly understood that where the compositions, systems, or methods use the term comprising, the specification also discloses the same compositions, systems, or methods using the term "consisting essentially of" and "consisting of" as it relates to the modified elements.

"Peptide," "protein," and "polypeptide" are used interchangeably to refer to a natural or synthetic molecule comprising two or more amino acids linked by the carboxyl group of one amino acid to the alpha amino group of another.

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers. As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., Type 1 diabetes). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection.

Glucose and $H_2O_2$-Responsive Nanoparticles

It is understood that the nanoparticles of the present disclosure can be used in combination with the various compositions, methods, products, kits, and applications disclosed herein.

A "smart", self-regulated, closed-loop drug (e.g., insulin) administration system would be highly desirable for the treatment of diabetes and other glucose regulation diseases. Disclosed herein is a glucose-responsive drug delivery nanoparticle having numerous advantageous properties, including but not limited to, producing $H_2O_2$ as a triggering response to high glucose levels (e.g., hyperglycemia), while also scavenging $H_2O_2$ from the system to avoid long-term biocompatibility issues. The polymeric nanoparticles (PVs) are self-assembled as a copolymer (e.g., block copolymer) and release entrapped cargo (e.g., therapeutic drug) in the presence of $H_2O_2$. The PVs are loaded with a glucose sensing enzyme (e.g., glucose oxidase (GOx)), which generates $H_2O_2$ from glucose oxidation. The PV scavenges $H_2O_2$ produced in the GOx-mediated response to hyperglycemia and, by virtue of the copolymer's sensitivity to $H_2O_2$, triggers nanoparticle disassembly and drug release. These features permit triggered drug delivery while reducing or avoiding peroxide-mediated tissue damage. The non-toxic PVs respond quickly to elevated glucose levels (e.g., within ten minutes), and the drug release rate increases with increasing glucose levels. Another important aspect of the disclosed PVs includes the ability to regulate glucose levels effectively while reducing the risk of hypoglycemia. Thus, the PVs deliver therapeutic agent when needed (e.g., during hyperglycemia), and refrain from doing so when released therapeutic agent may be undesirable or detrimental (e.g., during normo- or hypoglycemia). Sensitivity of PVs to $H_2O_2$ is also directly proportional to $H_2O_2$ concentrations, thus providing a means of further control over drug delivery by altering levels of GOx within the PVs. PVs can be integrated with a transcutaneous microneedle (MN) array patch to achieve a fast response, excellent biocompatibility, and pain-less administration.

In one aspect, disclosed herein is a nanoparticle comprising a copolymer. The copolymer comprises a polyethylene glycol polymer, a polyhydroxylated polymer, and a peroxide-sensitive pendant group. The nanoparticle further comprises a glucose-responsive agent. The nanoparticle also comprises a therapeutic agent. The copolymer of the nanoparticle encapsulates the glucose-responsive agent and the therapeutic agent.

As used herein, the terms "vesicle," "polymeric vesicle (PV)," and "nanoparticle" are used interchangeably with equivalent meanings. It is intended that where one of these terms is recited herein (e.g., vesicle), the interchangeable terms (e.g., polymeric vesicle, PV, nanoparticle) can be unequivocally substituted without any change in meaning.

The nanoparticle comprises a copolymer. The copolymer comprises at least two polymers, but in some embodiments can comprise at least three, at least four, or at least five polymers. The molecular weight of the copolymer can be at least 1,000 Da. In some embodiments, the molecular weight of the copolymer can be at least 10,000 Da, at least 20,000 Da, at least 30,000 Da, at least 40,000 Da, at least 50,000 Da, at least 75,000 Da, at least 100,000 Da, at least 150,000 Da, or at least 200,000 Da.

The arrangement of monomers within the copolymer is not strictly limited. For instance, the monomeric units of a first polymer (e.g., the polyethylene glycol polymer) can be integrated in an alternating, statistical, or random arrangement with monomeric units of a second polymer (e.g., the polyhydroxylated polymer). However, certain orientations of blocks of monomers can facilitate self-assembly of the copolymer into vesicles. Thus, in some embodiments, the copolymer can comprise a block copolymer. Each polymer block can, in some embodiments, be a homopolymer or, alternatively, contain additional monomeric units which disrupt homogeneity of the polymer. In some embodiments, the copolymer comprises a first homopolymer covalently linked to a second homopolymer.

The copolymer comprises a polyethylene glycol (PEG) polymer. The PEG polymer can contain modifications, for example, to attach pendant groups (e.g., a peroxide-sensitive pendant group). In some embodiments, the PEG is methoxylated. The PEG polymer comprises at least five ethylene glycol monomers. In some embodiments, PEG polymer comprises at least 10, at least 15, at least 20, at least 25, at least 30, at least 35, at least 40, at least 45, at least 50, at least 75, or at least 100 ethylene glycol monomers.

The copolymer comprises a polyhydroxylated polymer. The polyhydroxylated polymer contains hydroxyl groups to which pendant groups (e.g., a peroxide-sensitive pendant group) can be attached. Typically, at least 50% of the monomers of the polyhydroxylated polymer are hydroxylated. In some embodiment, at least 60%, at least 70%, at least 80%, at least 90%, at least 95%, or at least 99% of the monomers of the polyhydroxylated polymer are hydroxylated. In some embodiments, the polyhydroxylated polymer is a homopolymer of hydroxylated monomers. The polyhydroxylated polymer comprises at least five hydroxylated monomers. In some embodiments, polyhydroxylated polymer comprises at least 10, at least 15, at least 20, at least 25, at least 30, at least 35, at least 40, at least 45, at least 50, at least 75, or at least 100 hydroxylated monomers.

The ratio of number of hydroxylated monomers to number of ethylene glycol monomers in the copolymer can range from about 1:1 to about 20:1 or more. In some embodiments, the ratio of number of hydroxylated monomers to number of ethylene glycol monomers in the copolymer is about 20:1 or less, about 10:1 or less, about 8:1 or less, about 6:1 or less, about 4:1 or less, about 3:1 or less, or about 2:1 or less. In some embodiments, the ratio of number of hydroxylated monomers to number of ethylene glycol monomers in the copolymer is about 1:1 or less, about 0.75:1 or less, about 0.5:1 or less, about 0.25:1 or less, about 0.1:1 or less, or about 0.05:1 or less. In some embodiments, the ratio of number of hydroxylated monomers to number of ethylene glycol monomers in the copolymer ranges from about 1:1 to about 2:1, from about 1.1:1 to about 1.9:1, from about 1.2:1 to about 1.8:1, or from about 1.3:1 to about 1.5:1.

The polyhydroxylated polymer can comprise any type of biocompatible monomer containing a hydroxyl group. In some embodiments, the polyhydroxylated polymer comprises a polyamino acid. In some embodiments, the polyamino acid comprises polytyrosine or polyserine. In some embodiments, the polyhydroxylated polymer comprises a mixture of tyrosine and serine amino acids.

The copolymer further comprises a peroxide-sensitive pendant group. In some embodiments, the peroxide-sensitive pendant group is attached to the polyhydroxylated polymer. However, the peroxide-sensitive pendant group can also be attached to the PEG polymer, or both the polyhydroxylated polymer and the PEG polymer. In some embodiments, the peroxide-sensitive pendant group is attached to the hydroxyl groups of the polyhydroxylated polymer. In some embodiments, the peroxide-sensitive pendant group is attached to the methoxy groups of a mPEG polymer. The peroxide-sensitive pendant group can be attached by any type of chemical bond suitable for attachment to a biocompatible copolymer. However, the peroxide-sensitive pendant group should be capable of detaching in the presence of peroxide. In some embodiments, the peroxide-sensitive pendant group is attached by a carbonate bond. For example, a carbonate bond can be formed by a covalent bond between the hydroxyl group of the polyhydroxylated polymer and the ester group of a phenylboronic ester.

The copolymer contains a sufficient amount of peroxide-sensitive pendant groups to scavenge peroxide molecules and/or to facilitate nanoparticle self-assembly. In some embodiments, the copolymer comprises a polymer (e.g., a PEG polymer or a polyhydroxylated polymer) having at least 20% of its monomers conjugated with a peroxide-sensitive pendant group. In some embodiments, the copolymer comprises a polymer having at least 40%, at least 50%, at least 60%, at least 70%, or at least 75% of its monomers conjugated with a peroxide-sensitive pendant group.

The peroxide-sensitive pendant group can comprise any molecule capable of binding a copolymer as a pendant group, is sufficiently biocompatible (e.g., is not significantly toxic to a subject administered with the nanoparticles), and is capable of binding peroxide. The peroxide-sensitive pendant group, in some embodiments, can comprise a boronic ester. In some embodiments, the peroxide-sensitive pendant group comprises a phenylboronic ester.

The peroxide-sensitive pendant group is also capable of peroxide-mediated detachment (e.g., chemical cleavage) from the copolymer. Upon exposure to peroxide, the peroxide-sensitive pendant group detaches from the copolymer, forming a peroxide-scavenging leaving group. This mechanism facilitates reduction in peroxide-mediated cellular and tissue damage in areas adjacent to a nanoparticle which produces hydrogen peroxide in hyperglycemic conditions.

Typically, the copolymer is soluble in water. Water solubility facilitates disassembly of the nanoparticle when the copolymer is exposed to peroxide and/or acidic pH. Attachment of one or more pendant groups can, in some embodiments, alter the water solubility of the copolymer. For example, attachment of a peroxide-sensitive pendant group (e.g., a phenylboronic acid) can alter the water solubility of the copolymer, for example, by increasing the amphiphilicity of the copolymer. Altered solubility can facilitate self-assembly of the copolymer into nanoparticles. As such, cleavage of such a pendant group can facilitate disassembly or degradation of the nanoparticle.

The nanoparticle further comprises a glucose-responsive agent. In some embodiments, the glucose-responsive agent comprises a pH-altering agent which reduces the pH upon exposure to glucose. In some embodiments, the glucose-responsive agent comprises a glucose-responsive enzyme. In some embodiments, the glucose-responsive agent comprises glucose oxidase (GOx). GOx oxidizes glucose to glucuronic acid, producing hydrogen peroxide as a byproduct of the reaction. GOx-mediated glucose oxidation also reduces the pH. In some embodiments, increased acidity can contribute to degradation of the copolymer, thereby facilitating release of encapsulated therapeutic agent. Further, peroxide produced via GOx-mediated glucose oxidation can be scavenged by the peroxide-sensitive pendant group, thereby facilitating detachment of the pendant group.

Without limitation and without wishing to be bound by any one theoretical mechanism, it is thought that elevated glucose levels facilitate increased glucose diffusion into the nanoparticle, thereby increasing the amount of glucose substrate for GOx-mediated glucose oxidation. As GOx oxidizes glucose, increasing amounts of peroxide are produced and the pH inside the lumen of the nanoparticle can decrease. The peroxide-sensitive pendant group scavenges released peroxide, resulting in detachment of the peroxide-sensitive pendant group from the copolymer. As the pH decreases and the peroxide-sensitive pendant group is cleaved, the nanoparticle disassembles, perhaps due to increased water solubility of the copolymer. Encapsulated therapeutic agent is thereby released from disassembled nanoparticles. In this manner, the nanoparticle delivers the therapeutic agent(s) in conditions of elevated glucose levels (e.g., hyperglycemia).

The nanoparticle further comprises a therapeutic agent. The therapeutic agent should be of sufficiently small size to fit within the lumen of the nanoparticle (in other words, to be encapsulated by the nanoparticle). In some embodiments, the therapeutic agent treats glucose imbalance and/or dysregulation. In some embodiments, the therapeutic agent treats diabetes (Type 1 and/or Type II). In some embodiments, the therapeutic agent stimulates tissue absorption and/or utilization of glucose. In some embodiments, the therapeutic agent comprises insulin or a biologically active compound derived from insulin. In some embodiments, the nanoparticle comprises a combination of therapeutic agents (e.g., two or more therapeutic agents).

In some embodiments, the nanoparticle can further contain an enzyme for scavenging metabolism-byproducts, for example a peroxide-metabolizing enzyme. For example, the nanoparticle can comprise an encapsulated enzyme which can degrade or scavenge hydrogen peroxide byproduct. In some embodiments, the peroxide-metabolizing enzyme can be catalase (CAT). CAT can be used as a complement to the peroxide-sensitive pendant group to temper the damaging effects of extensive peroxide production, for example in very high hyperglycemic conditions. An amount of CAT can be used which does not interfere with the peroxide-mediated detachment of the peroxide-sensitive pendant group from the copolymer. Catalase can provide a further benefit to GOx-mediated glucose oxidation in that catalase can regenerate oxygen to facilitate further glucose oxidation.

As used herein, "hyperglycemic levels of glucose" refer to concentrations of glucose which cause, or are at risk of causing, clinical hyperglycemia. Strict cutoff values for hyper-, normo-, and hypoglycemia can vary between subjects, particularly between subjects with varying forms or degrees of severity of diabetes. In some embodiments, a hyperglycemic level of glucose comprises greater than 100 mg/dL glucose. In some embodiments, a hyperglycemic level of glucose comprises 125 mg/dL or greater, 150 mg/dL or greater, 175 mg/dL or greater, or 200 mg/dL glucose or greater. Conversely, "normoglycemic levels of glucose" refer to concentrations of glucose which are typical/normal and are not usually known to relate to clinical conditions (or severe clinical conditions) of glycemic imbalance. In some embodiments, a normoglycemic level of glucose comprises from about 70 mg/dL glucose to less than 200 mg/dL glucose. In some embodiments, a normoglycemic level of glucose comprises from about 70 mg/dL glucose to about 175 mg/dL glucose, from about 70 mg/dL glucose to about 150 mg/dL glucose, from about 70 mg/dL glucose to about 125 mg/dL glucose, or from about 70 mg/dL glucose to about 100 mg/dL glucose. A "hypoglycemic level of glucose" refers to a concentration of glucose which causes, or is at risk of causing, clinical hypoglycemia. In some embodiments, a hypoglycemic level of glucose comprises 70 mg/dL glucose or less. In some embodiments, a hypoglycemic level of glucose comprises 60 mg/dL or less, 50 mg/dL or less, 40 mg/dL or less, or 30 mg/dL glucose or less. In some embodiments, a hyperglycemic level of glucose comprises 200 mg/dL or more glucose, a normoglycemic level of glucose comprises from about 70 mg/dL glucose to less than 200 mg/dL glucose, and a hypoglycemic level of glucose comprises less than about 70 mg/dL glucose.

The nanoparticle typically has a diameter within the nm range (i.e. from about 1 to about 1,000 nm). However, the nanoparticle is not per se limited to the nm size range, and can be, for instance, greater than 1,000 nm in diameter (e.g., up to 1,500 nm, up to 2,000 nm, or up to 3,000 nm or more). In some embodiments, the nanoparticle has a diameter of 1,000 nm or less, 750 nm or less, 500 nm or less, 400 nm or less, 300 nm or less, or 200 nm or less. In some embodiments, the nanoparticle has a diameter from 10 nm to less than 1,000 nm. Optionally, the nanoparticle has a diameter from 100 nm to 800 nm, from 100 nm to 600 nm, from 100 nm to 400 nm, or from 150 nm to 250 nm. It is understood that the nanoparticle can have a diameter ranging from any of the minimum values to any of the maximum values described above. For example, the nanoparticle can have a diameter ranging from 100 nm to 1,000 nm, or from 1 nm to 500 nm, etc.

The therapeutic agent encapsulation efficiency of the nanoparticle can vary. Encapsulation efficiencies are generally calculable based on the amount of therapeutic agent used in the encapsulation procedure and the amount of therapeutic agent which remains in solution after the nanoparticles are removed from the encapsulation solution. The nanoparticle can have an encapsulation efficiency of 50% or greater of the therapeutic agent. In some embodiments, the nanoparticle has an encapsulation efficiency of 60% or greater, 70% or greater, 75% or greater, 80% or greater, or 82% or greater of the therapeutic agent.

The nanoparticles can be further defined by the amount (by weight) of encapsulated therapeutic agent per amount (by weight) of nanoparticle, referred to as the therapeutic agent loading percentage. Typically, the therapeutic agent loading percentage is at least 1%, but this percentage can be lower depending on the type, size, and effective dose of the therapeutic agent. In some embodiments, the therapeutic agent loading percentage is at least 5%, at least 10%, or at least 12% or more.

The nanoparticle is configured such that the copolymer of the nanoparticle encapsulates the glucose-responsive agent and the therapeutic agent. By "encapsulated," it is meant there is a physical encasing of the contents (e.g., the glucose-responsive agent and the therapeutic agent) in the nanoparticle, such that the contents generally do not escape or diffuse out from the nanoparticle. In some embodiments, the copolymer encapsulates the contents, but permits diffusion of glucose into the lumen of the nanoparticle. When the nanoparticle disassembles, the contents are no longer "encapsulated" and can be released from the lumen of the nanoparticle.

Optionally, the nanoparticle can be formulated in a medicament. The nanoparticle can be formulated in any suitable medicament including, for example, but not limited to, solids, semi-solids, liquids, and gaseous (inhalant) dosage forms, such as tablets, pills, powders, liquid solutions or suspensions, suppositories, injectables, infusions, inhalants, hydrogels, topical gels, hydrogels, sprays, and the like. Optionally, the medicament comprises a pharmaceutically acceptable excipient/carrier. Optionally, the medicament comprises an effective dose of the therapeutic agent (e.g., a dose effective to correct glucose imbalance or dysregulation).

Also disclose herein is a device comprising a plurality of microneedles each having a base end and a tip; a substrate to which the base ends of the microneedles are attached; and a plurality of nanoparticles comprising a copolymer comprising a polyethylene glycol polymer, a polyhydroxylated polymer, and a peroxide-sensitive pendant group; a glucose-responsive agent; and a therapeutic agent; wherein the copolymer encapsulates the glucose-responsive agent and the therapeutic agent. The nanoparticle can be any herein disclosed nanoparticle within the spirit of the invention. The device can be a patch, for example a transcutaneous patch, comprising microneedles (MN) which insert into the dermis of a subject. The patch is typically made out of non-toxic, biocompatible materials (e.g., hyaluronic acid), and can provide for rapid and low/no pain administration of nanoparticles.

In some embodiments, the microneedles comprise hyaluronic acid. In addition to hyaluronic acid, the microneedles may also comprise a variety of materials, including metals, ceramics, semiconductors, organics, polymers, composites, or a combination thereof. Typical materials of construction include pharmaceutical grade stainless steel, gold, titanium, nickel, iron, tin, chromium, copper, palladium, platinum, alloys of these or other metals, silicon, silicon dioxide, and polymers. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone).

The microneedles should have the mechanical strength to remain intact while being inserted into the biological barrier, while remaining in place for up to a number of days, and while being removed. In some embodiments, the microneedle must remain intact at least long enough for the microneedle to serve its intended purpose (e.g., delivery of the therapeutic agent). In some embodiments, the microneedles have a mechanical strength of at least 1 Newton (N) per needle, at least 2 N/needle, or at least 3 N/needle.

The microneedles can have straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, i.e. they may simply be cylinders with blunt or flat tips.

The microneedles can be oriented perpendicular or at an angle to the substrate. In one embodiment, the microneedles are oriented perpendicular to the substrate so that a larger density of microneedles per unit area of substrate can be provided. An array of microneedles can include a mixture of microneedle orientations, heights, or other parameters.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape.

The cross-sectional dimensions can be between about 1 μm and 1000 μm, such that the base can be about 100-500 μm, and the tip can be between 1 and 20 μm. In one embodiment, the microneedle can be approximately 300 μm at the base, and approximately 5 μm at the tip.

The length of the microneedles typically is between about 10 μm and 1 mm, preferably between 400 μm and 1 mm. In one embodiment, the length (or height) of the microneedle is about 600 μm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles. In one embodiment, the microneedles are arranged in a 15 by 15 array with 600 μm tip-to-tip spacing. In one embodiment, the microneedles are arranged in a 20 by 20 array with 600 μm tip-to-tip spacing.

The shell of the microneedle can be considered as the outside portion of the microneedle that comes into contact with the subject. The core or the microneedle can be considered as the portion of the microneedle located toward the center of each microneedle and is separated from contacting the subject's skin by the shell portion of the microneedle.

In some embodiments, the nanoparticles are formulated in a hydrogel. In some embodiments, the hydrogel is coated onto the MNs of a patch. In some embodiments, the plurality of microneedles are arranged on a patch having a size of 500 mm$^2$ or less, 250 mm$^2$ or less, or 100 mm$^2$ or less. In some embodiments, the plurality of microneedles have a center-to-center interval of about 200 µm to about 800 µm. In some embodiments, the plurality of microneedles have a height from about 100 nm to 1.8 µm, from about 300 to about 1,000 nm, or from about 400 to about 700 nm. In some embodiments, the plurality of microneedles have a height of about 600 nm.

Methods of Use

Also disclosed herein are methods of delivering a therapeutic agent to a subject comprising (a) administering to the subject a nanoparticle comprising a copolymer comprising a polyethylene glycol polymer, a polyhydroxylated polymer, and a peroxide-sensitive pendant group; a glucose-responsive agent; and a therapeutic agent; wherein the copolymer encapsulates the glucose-responsive agent and the therapeutic agent; and (b) releasing the therapeutic agent from the nanoparticle in the presence of hyperglycemic levels of glucose.

Each of the herein disclosed methods can include any herein disclosed nanoparticle within the spirit of the invention.

The subject can be any mammalian subject, for example a human, dog, cow, horse, mouse, rabbit, etc. In some embodiments, the subject has a glucose dysregulation condition (e.g., glycemic imbalance). In some embodiments, the subject has hyperglycemia. In some embodiments, the subject has diabetes (Type 1 or Type 2).

The administering step can be performed by any method suitable to administer the herein disclosed nanoparticles to a subject. The nanoparticles can be administered systemically (e.g., by injection) or locally. In some embodiments, the nanoparticle is administered transcutaneously. In some embodiments in which the nanoparticles are administered locally (e.g., by local transcutaneous patch), the nanoparticles exert systemic effects on blood glucose levels.

The administering step can include at least one, at least two, at least three, at least four, at least five, at least six, at least seven, at least eight, at least nine, or at least ten dosages. The administering step can be performed before the subject exhibits disease symptoms (e.g., prophylactically), or during or after disease symptoms occur. The administering step can be performed prior to, concurrent with, or subsequent to administration of other agents to the subject. In some embodiments, the administering step is performed prior to, concurrent with, or subsequent to the administration of one or more additional diagnostic or therapeutic agents. In some embodiments, the administering step is performed as needed, for example, when the subject experiences hyperglycemia or is at risk of becoming hyperglycemic.

In some embodiments, the nanoparticle is administered in a hydrogel. In some embodiments, the nanoparticle is administered in a device (e.g., a transcutaneous patch) comprising a plurality of microneedles each having a base end and a tip; and a substrate to which the base ends of the microneedles are attached. In some embodiments, the device provides quick and low/no pain administration of the nanoparticles. In some embodiments, the device produces small wounds which heal to closing within 6 hours or less.

The methods include releasing the therapeutic agent from the nanoparticle in the presence of hyperglycemic levels of glucose. In some embodiments, hyperglycemic levels of glucose facilitate disassembly of the nanoparticle, thereby facilitating release of the therapeutic agent. In some embodiments, glucose is oxidized to glucuronic acid by the glucose-responsive agent, producing peroxide as a byproduct. In some embodiments, peroxide production facilitates a decrease in the pH in the nanoparticle lumen. In some or further embodiments, the peroxide is scavenged by the peroxide-sensitive pendant group.

In some embodiments, the method further comprises detaching the peroxide-sensitive pendant group from the copolymer upon exposure to the peroxide. In such embodiments, it is believed that peroxide produced by the glucose-responsive agent facilitates cleavage/detachment of the peroxide-sensitive pendant group from the copolymer. In some embodiments, the detaching step facilitates disassembly of the nanoparticle, thereby releasing the therapeutic agent from the nanoparticle.

In some embodiments, the method further comprises correcting glycemic imbalance, for example by reducing blood glucose levels. In some embodiments, the therapeutic agent comprises insulin. In some embodiments, the method reduces blood glucose levels from hyperglycemic levels to normoglycemic levels. The method can also avoid resulting in hypoglycemia. Thus, in some embodiments, the blood glucose levels are reduced to no lower than normoglycemic levels. For example and without limitation, the nanoparticle can terminate or significantly reduce the rate of glucose oxidation, or of peroxide production, when normoglycemic levels of glucose are achieved. Similarly, in some embodiments, the therapeutic agent releasing step can occur at a time which is delayed after the nanoparticle administering step. For example, the nanoparticle can be administered prophylactically to a subject having hypo- or normoglycemia, under which conditions the nanoparticles do not reduce glucose levels. However, when the subject subsequently becomes hyperglycemic, the therapeutic agent releasing step can initiate, thereby reducing glucose levels in some embodiments.

The methods can reduce blood glucose levels, or maintain normoglycemia, for a period of time which is longer than that provided by non-encapsulated insulin. In some embodiments, the methods maintain normoglycemia for at least one hour, at least two hours, at least three hours, at least four hours, or at least five hours.

The herein disclosed methods can avoid peroxide-mediated tissue damage. Upon exposure to peroxide, the peroxide-sensitive pendant group detaches from the copolymer, forming a peroxide-scavenging leaving group. This mechanism facilitates reduction in peroxide-mediated cellular and tissue damage in areas adjacent to a nanoparticle which produces hydrogen peroxide in hyperglycemic conditions.

Also disclosed herein are methods of normalizing (e.g., reducing) blood glucose levels in a subject comprising (a) administering to the subject a nanoparticle comprising a copolymer comprising a polyethylene glycol polymer, a polyhydroxylated polymer, and a peroxide-sensitive pendant group; a glucose-responsive agent; and a therapeutic agent; wherein the copolymer encapsulates the glucose-responsive agent and the therapeutic agent; and (b) releasing the therapeutic agent from the nanoparticle in the presence of hyperglycemic levels of glucose.

Also disclosed herein are methods of regulating insulin delivery in a subject comprising (a) administering to the subject a nanoparticle comprising a copolymer comprising a polyethylene glycol polymer, a polyhydroxylated polymer, and a peroxide-sensitive pendant group; a glucose-responsive agent; and insulin; wherein the copolymer encapsulates the glucose-responsive agent and insulin; and (b) releasing insulin from the nanoparticle in the presence of hyperglycemic levels of glucose.

Kits

Also disclosed herein are kits comprising a nanoparticle comprising a copolymer comprising a polyethylene glycol polymer, a polyhydroxylated polymer, and a peroxide-sensitive pendant group; a glucose-responsive agent; and a therapeutic agent; wherein the copolymer encapsulates the glucose-responsive agent and the therapeutic agent; and a device for administering the nanoparticle.

In any of the kits disclosed herein, the nanoparticle can be any herein disclosed nanoparticle within the spirit of the invention. Similarly, the kit can be used to administer the nanoparticle to any herein disclosed subject, particularly a human.

The kit comprises a device for administering nanoparticles. The device, in some embodiments, is configured for transcutaneous administration. In some embodiments, the device comprising a plurality of microneedles each having a base end and a tip; and a substrate to which the base ends of the microneedles are attached. The device further comprises any herein disclosed nanoparticle within the spirit of the invention. In some embodiments, the device provides a plurality of nanoparticles and a pharmaceutically acceptable carrier. The device can be a patch, for example a transcutaneous patch, comprising microneedles (MN) which insert into the dermis of a subject. The patch is typically made out of non-toxic, biocompatible materials (e.g., hyaluronic acid), and can provide for rapid and low/no pain administration of nanoparticles.

In some embodiments, the nanoparticles are formulated in a hydrogel. In some embodiments, the hydrogel is coated onto the MNs of a patch. In some embodiments, the plurality of microneedles are arranged on a patch having a size of 500 mm$^2$ or less, 250 mm$^2$ or less, or 100 mm$^2$ or less. In some embodiments, the plurality of microneedles have a center-to-center interval of about 200 μm to about 800 μm. In some embodiments, the plurality of microneedles have a height from about 100 nm to 1.8 μm, from about 300 to about 1,000 nm, or from about 400 to about 700 nm. In some embodiments, the plurality of microneedles have a height of about 600 nm. In some embodiments, the microneedles have a mechanical strength of at least 1 Newton (N) per needle, at least 2 N/needle, or at least 3 N/needle.

A number of embodiments of the invention have been described. Nevertheless, it will be understood that various modifications may be made without departing from the spirit and scope of the invention. Accordingly, other embodiments are within the scope of the following claims.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be solely as examples of the invention and are not intended to limit the scope of what the inventors regard as their disclosure. These examples are not intended to exclude equivalents and variations of the present invention which are apparent to one skilled in the art. Unless indicated otherwise, temperature is ° C. or is at ambient temperature, pressure is at or near atmospheric, and other conditions are understood to be standard conditions. There are numerous variations and combinations of process conditions that can be used to optimize product quality and performance. Only reasonable and routine experimentation will be required to optimize such process conditions.

Example 1: $H_2O_2$-Responsive Nanoparticles Integrated with Transcutaneous Patches for Glucose-Mediated Insulin Delivery.

Figure 1B:
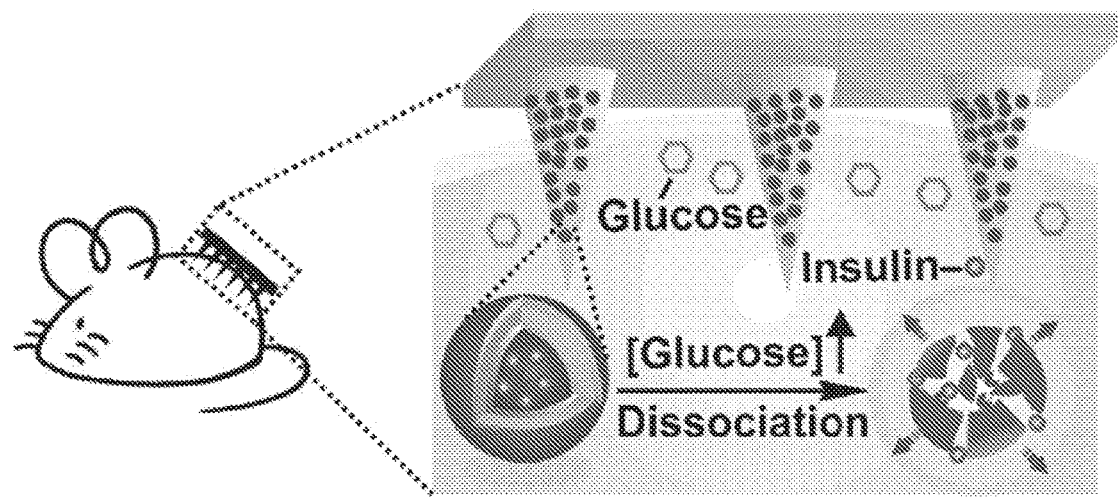

PVs, also known as polymersomes, are usually self-assembled from amphiphilic block copolymers to form hollow structures consisting of an aqueous core and a polymer bilayer membrane. See Tanner, et al., *Acc. Chem. Res.*, 2011, 44:1039. PVs hold great promise for controlled drug delivery due to their robust structures and large loading capacity of hydrophilic molecules. Here, the PVs are self-assembled from block copolymer incorporated with poly-ethylene glycol (PEG) and phenylboronic ester (PBE)-conjugated polyserine (designated mPEG-b-P(Ser-PBE)) and have hollow spherical structures with GOx and insulin encapsulated in the interior. The pendant PBE was selected for its facile $H_2O_2$-mediated degradation at physiological conditions (FIG. 1A and 1B). See Broaders, et al., *J. Am. Chem. Soc.*, 2010, 133:756; de Gracia Lux, et al., *J. Am. Chem. Soc.*, 2012, 134:15758. For in vivo applications, nanoparticles were further integrated with transcutaneous microneedle-array patch. Microneedles, which typically have needle lengths shorter than one millimeter, have become an attractive transcutaneous drug delivery technology due to ease of use and improved patient compliance. Cross-linked hyaluronic acid (HA) was chosen to prepare the microneedles to achieve excellent biocompatibility and sufficient stiffness. See Gittard, et al., *J. Adhes. Sci. Technol.*, 2013, 27:227. When the microneedle patch was applied to diabetic mice, glucose diffused across the membrane and interacted with GOx in the cavity, leading to oxidation of glucose to gluconic acid, simultaneously generating $H_2O_2$:

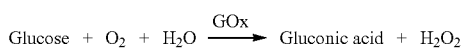

$$\text{Glucose} + O_2 + H_2O \xrightarrow{\text{GOx}} \text{Gluconic acid} + H_2O_2$$

See Yu, et al., *Proc. Natl. Acad. Sci.*, 2015, 112:8260. By virtue of generated $H_2O_2$, the copolymer mPEG-b-P(Ser-PBE) loses its PBE side chains and becomes water soluble, thereby leading to disassembly of the PVs and subsequent release of pre-loaded insulin. The transcutaneous device provides a desirable smart insulin delivery system with high drug loading capacity, fast response, and painless administration.

Results

FIG. 1A shows the concept underlying $H_2O_2$-responsive nanoparticles for glucose-mediated insulin release. A deblock copolymer comprised of a PEG polymer and polyserine containing phenylboronic ester (PBE) pendant groups (mPEG-b-P(Ser-PBE)) self-assembles into a polymeric vesicle (PV). During the assembly process, glucose oxidase (GOx) and insulin can be entrapped in the formed PV. As glucose concentrations rise to hyperglycemic levels, increased glucose diffusion into the vesicle results in increased glucose oxidation by GOx, resulting in increased $H_2O_2$ production. Phenylboronic esters (PBE) scavenge produced $H_2O_2$ molecules, resulting in cleavage of PBE from the copolymer and subsequent nanoparticle degradation, thereby releasing entrapped insulin. FIG. 1B shows a microneedle patch decorated with nanoparticles, which can be applied to the skin of diabetic mice to deliver nanoparticles transcutaneously.

Figure 2A:
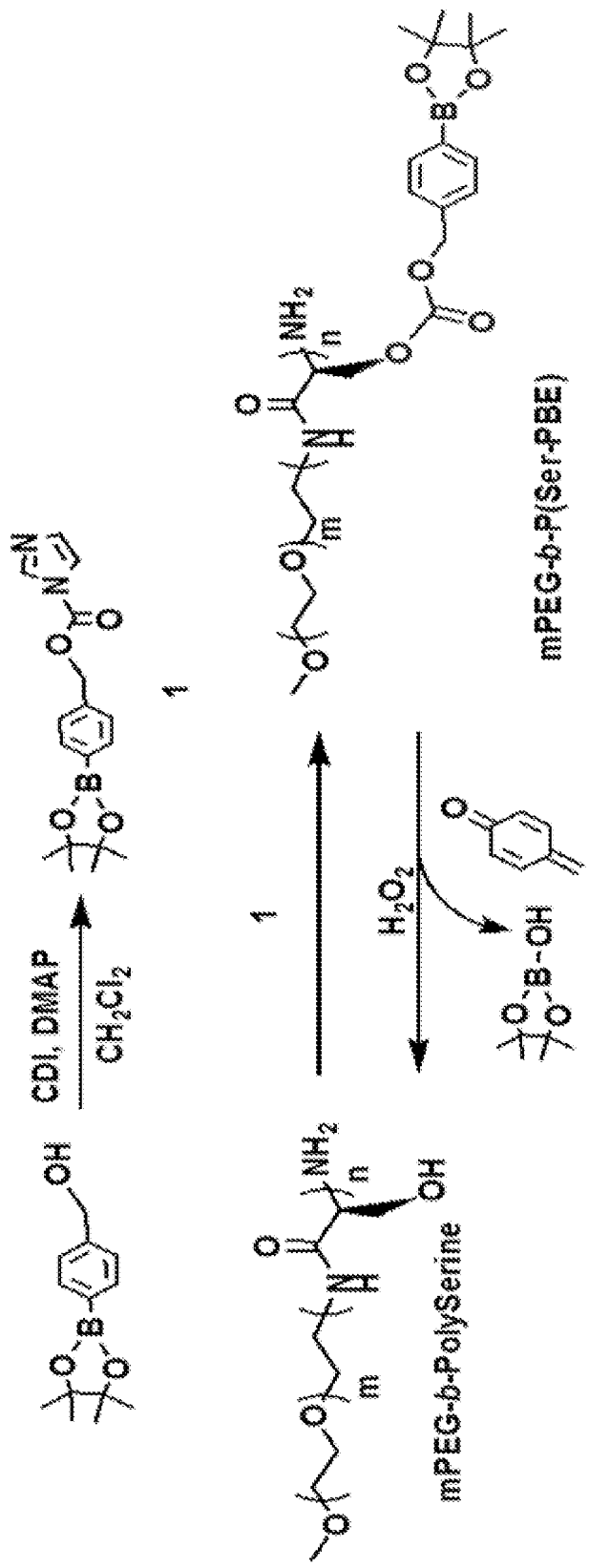
FIGS. 2A-B depict chemical construction of mPEG-b-P (Ser-PBE).
Figure 2B:
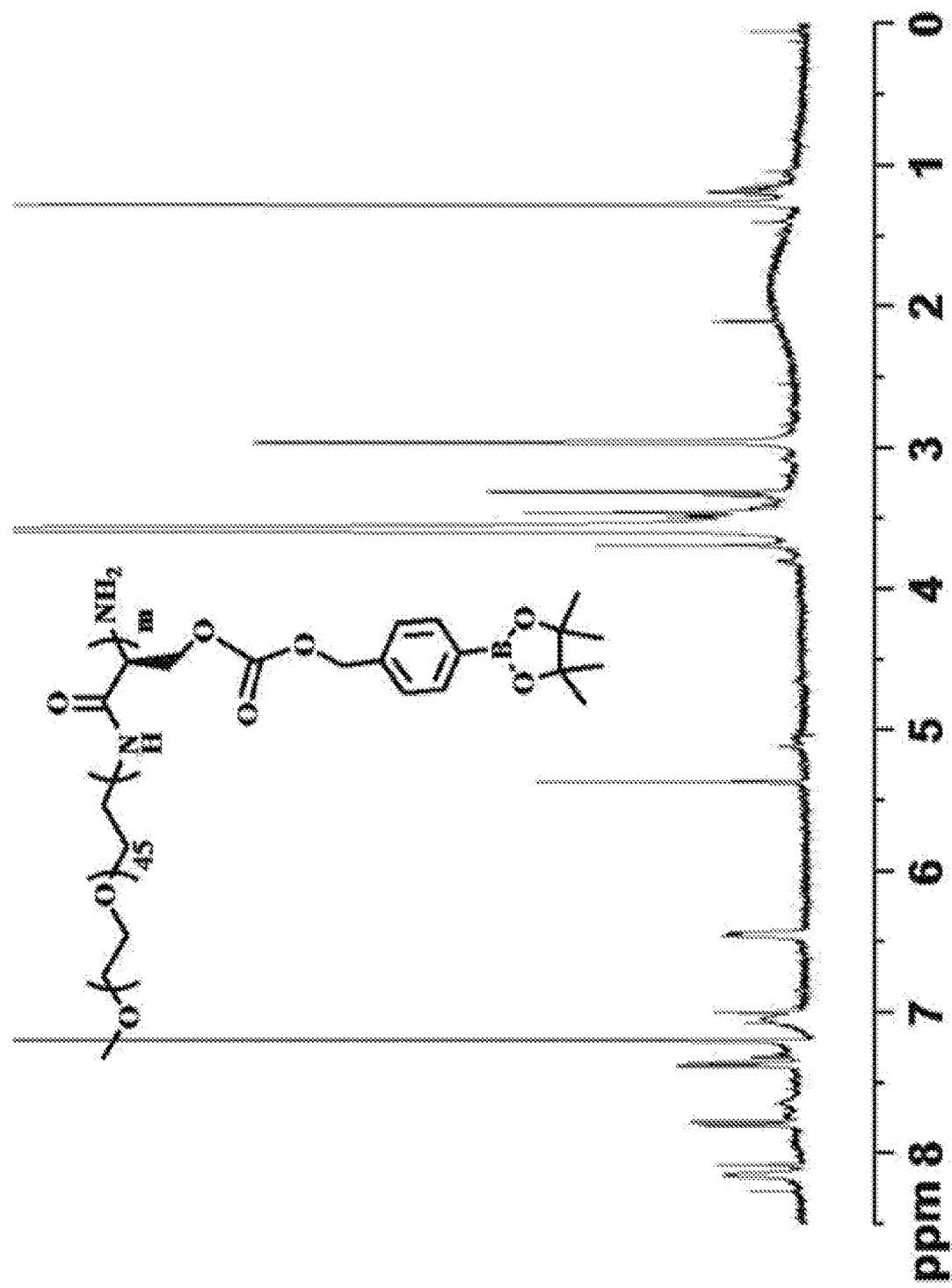

The diblock copolymer (mPEG-β-Polyserine) was first synthesized via the amine-initiated ring-opening polymerization (ROP) of N-carboxy-α-amino acid anhydrides (NCA) of serine. See Tai, et al., *Biomacromolecules*, 2014, 15:3495; Lu, et al., *Nat. Commun.*, 2011, 2:206; Wang, et al., *J. Am. Chem. Soc.*, 2011, 133:12906. 4-(Hydroxymethyl) phenylboronic acid pinacol ester (PBE) was then conjugated to the pendant hydroxyl groups of the serine residue via a carbonate linkage (FIG. 2A). The polymerization degree of the polyserine block was calculated to be 60, after which 75% of serine side-chain hydroxyl groups were conjugated with PBE, determined by using $^1$H NMR peak area with the methylene peak of mPEG as a standard (FIG. 2B). The hydrophobic PBE groups have at least three main functions: 1) to scavenge $H_2O_2$, 2) to change the solubility of the polymer and enable the formation of PVs in the aqueous solution, and: 3) to provide facile $H_2O_2$-mediated dissociation of PVs for rapid release of insulin (FIG. 1A).

Figure 3A:
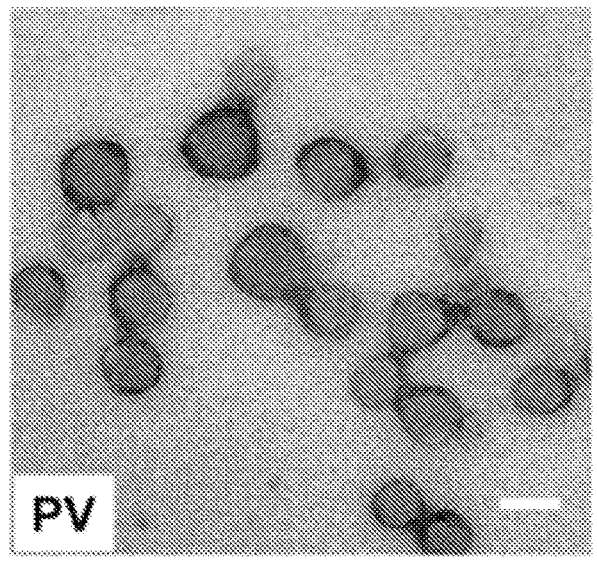
FIGS. 3A-C depict size characterization of glucose-responsive polymer nanoparticles (PVs).
Figure 3B:
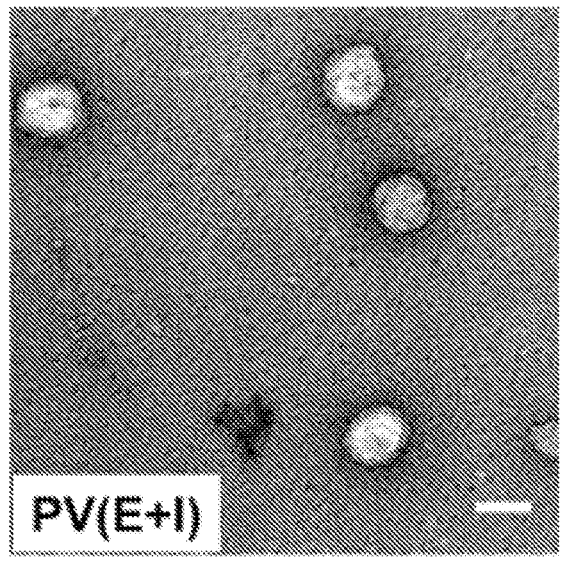
Figure 3C:
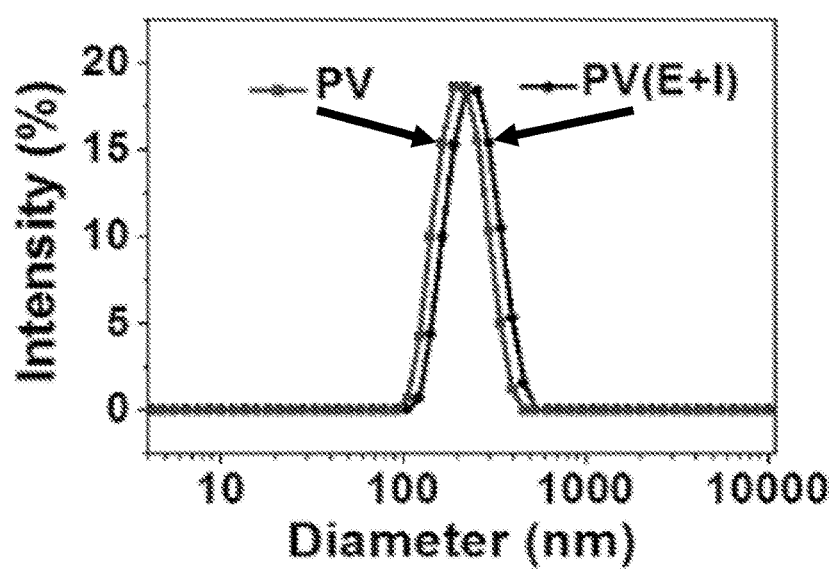
Figure 4:
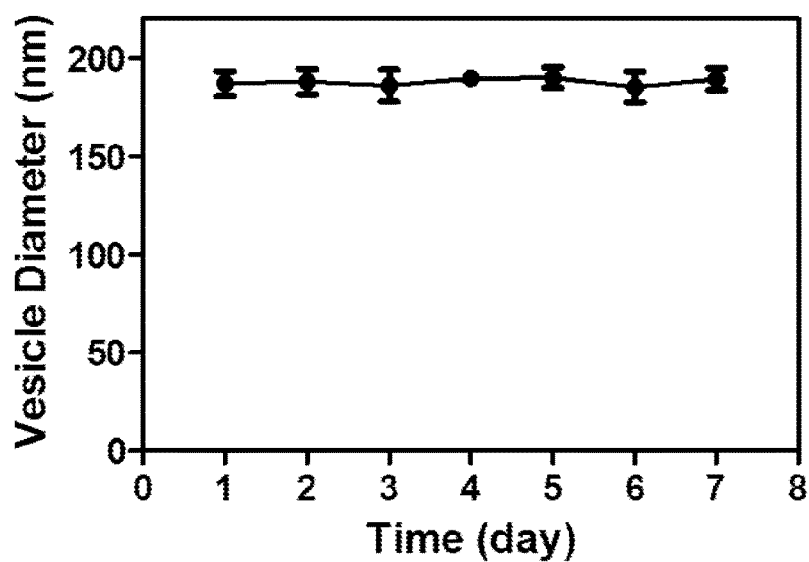
FIG. 4 is a graph depicting stability of PVs in PBS at room temperature, as determined by DLS.

Self-assembly of the resultant diblock copolymer mPEG-b-P(Ser-PBE) was conducted using a solvent evaporation method. Morphology of resultant PVs was characterized by transmission electron microscopy (TEM) and dynamic light scatting (DLS). TEM images showed spherical polymeric nanoparticles (PVs) with hollow structures were obtained (FIG. 3A). The average diameter of empty PVs was determined by DLS to be about 200 nm (FIG. 3C). The stability of empty PVs was confirmed by DLS. No significant diameter change was observed for over 1 week at 4° C. (FIG. 4).

The PVs were then constructed to encapsulate GOx enzyme (E) and insulin (I). TEM imaging shows that the cavity of PVs was filled after encapsulating GOx and insulin (PVs(E+I)) (FIG. 3B). Further, DLS showed the average diameter increased to 220 nm (FIG. 3C), consistent with TEM-determined filling of nanoparticles. The zeta-potentials of PVs and PVs(E+I) were measured to be −14.4 and −14.1 mV, respectively.

Figure 5A:
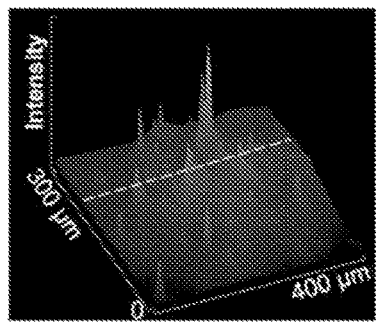
FIGS. 5A-F depict encapsulation of fluorescently labeled insulin and release thereof in hyperglycemic levels of glucose in vitro. GOx enzyme (E) and FITC-labeled insulin were encapsulated in PVs. 2.5D fluorescence images of PV(E+I) solution were taken pre-incubation (FIG. 5A) and post-incubation in 400 mg/dL glucose solution for 1 hour (FIG. 5B) and 2 hours (FIG. 5C) at 37° C., respectively. Fluorescence intensity distributions shown in FIGS. 5A-C along the indicated white dash line were calculated and plotted in arbitrary unit (a.u.) for pre-incubation (FIG. 5D) and post-incubation in glucose for 1 hour (FIG. 5E) and 2 hours (FIG. 5F), respectively.

To further demonstrate insulin encapsulation, FITC-labeled insulin was loaded into PVs. Spiculate clusters in fluorescence images of PVs confirmed successful encapsulation of FITC-labeled insulin (FIG. 5A). The insulin loading content of PVs was determined to be 12.5±0.5% (wt/wt) and loading efficiency was 82.5±1.0%.

The $H_2O_2$-responsive capability of insulin-loaded nanoparticles was shown by incubating the nanoparticles in PBS buffer with different $H_2O_2$ concentrations (0, 50, 200 μM). Increased insulin release occurred with increasing $H_2O_2$ concentrations (FIG. 6).

Figure 5B:
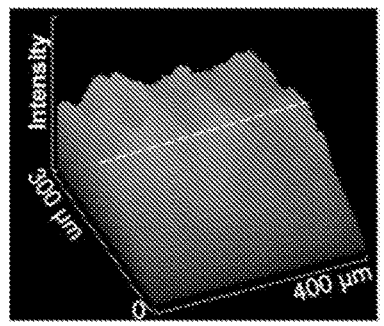
Figure 5C:
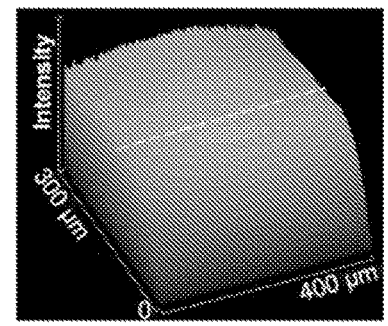
Figure 5D:
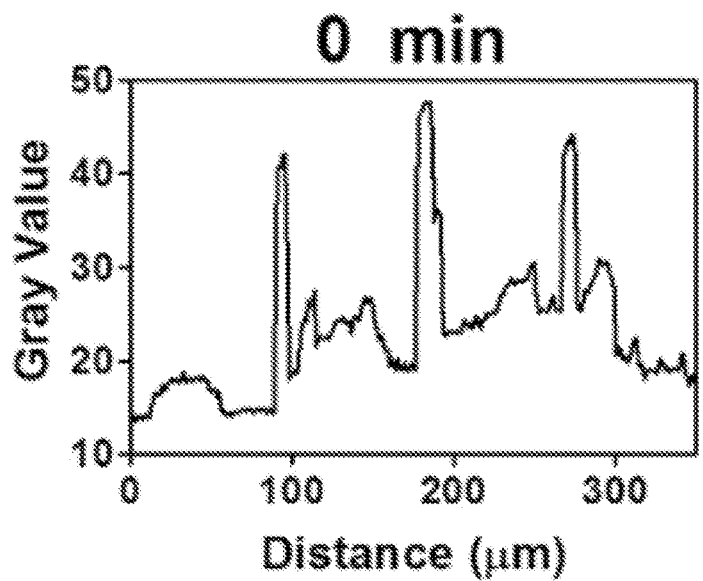
Figure 5E:
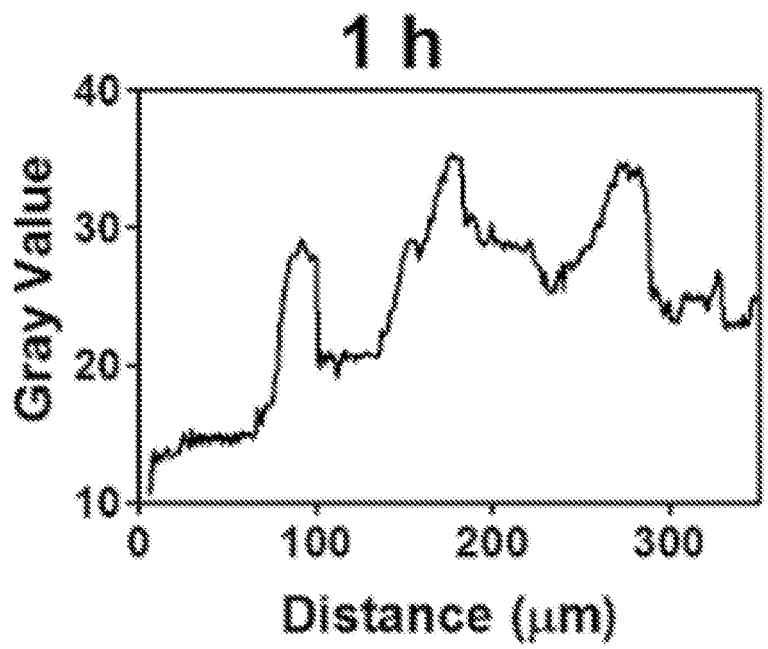
Figure 5F:
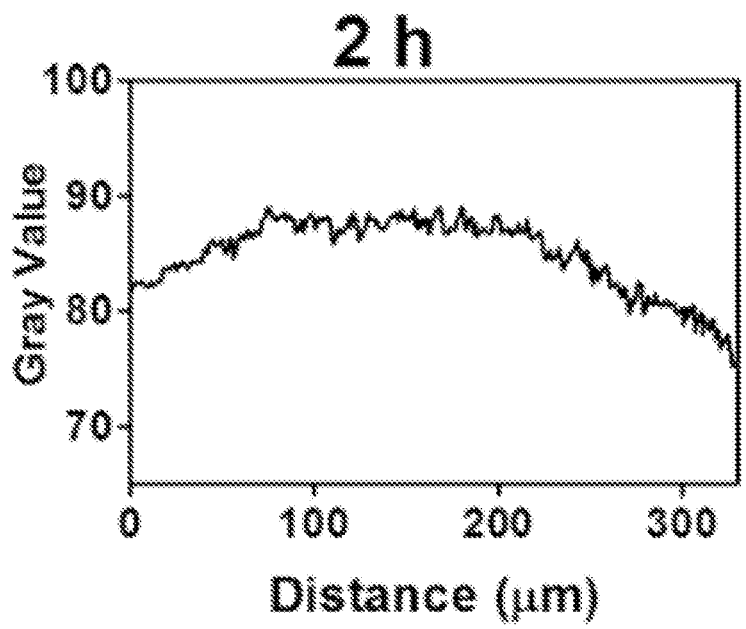

$H_2O_2$-responsive disassembly of PVs mediated by glucose was examined by incubating the nanoparticles in PBS buffer at a glucose concentration of 400 mg/dL, a typical hyperglycemic level, and observing corresponding size changes. As discussed above, fluorescence signals showed PVs with encapsulated FITC-insulin had a spiculate cluster signal prior to exposure to hyperglycemic levels of glucose (FIG. 5A). However, addition of 400 mg/dL glucose caused swelling of the clusters within one hour (FIG. 5B), and became more homogeneous by two hours (FIG. 5C). Quantification of fluorescence signals over time are shown in FIGS. 5D-F, corresponding to the fluorescence graphs shown at times zero, one, and two hours of FIGS. A-C, respectively. Quantified results further show homogenization of FITC-insulin clusters upon exposure to glucose. These results verified disassembly of the PVs and subsequent FITC-insulin release.

Figure 7C:
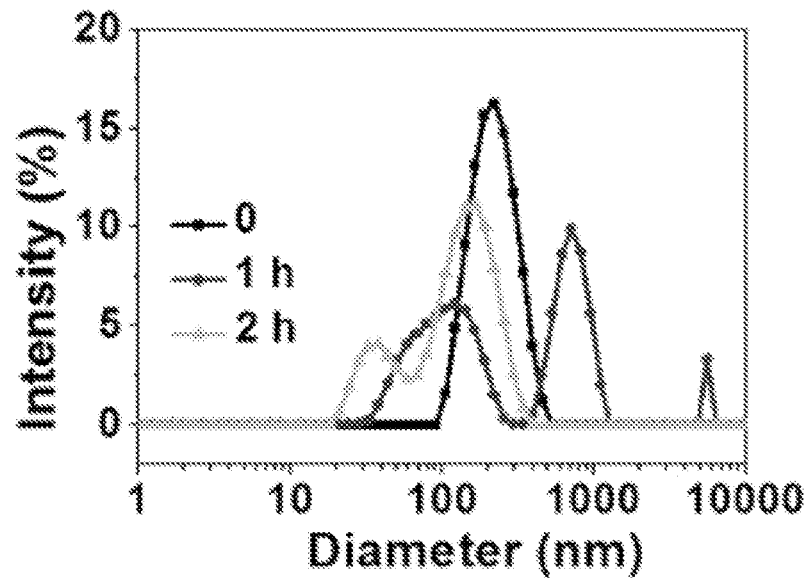

Morphology changes in PVs encapsulating GOx and insulin were analyzed in response to glucose exposure. After incubation in a solution of 400 mg/dL glucose for one hour, TEM images showed PV structures became dissociated, and some PVs recombined into large and small particles (FIG. 7A). After two hours of glucose exposure, both nanoparticle density (population per unit area) and size were further reduced, and a large amount of cargo leakage was observed (FIG. 7B). Nanoparticle diameters measured by DLS quantified diameter changes in PVs over time in response to glucose exposure (FIG. 7C).

Figure 8A:
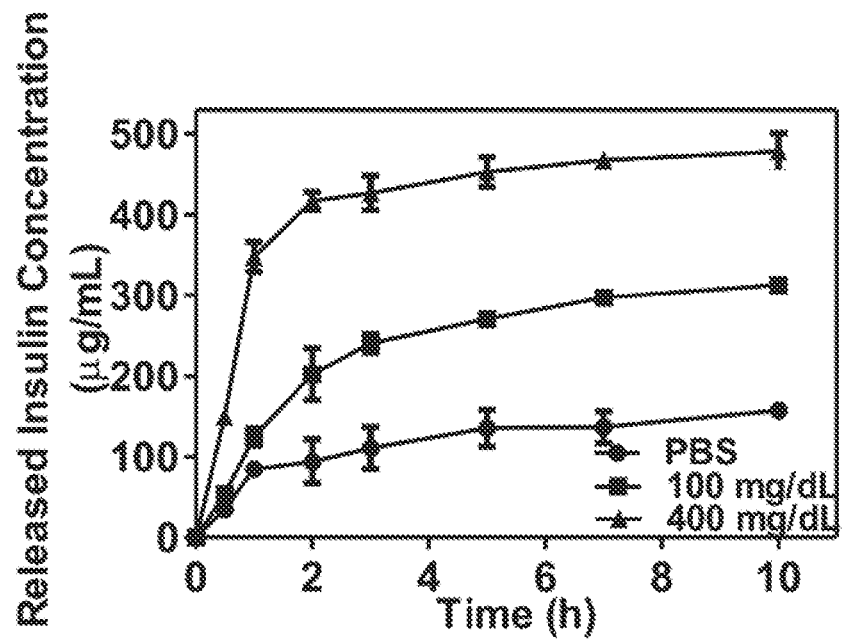
FIGS. 8A-D are graphs showing insulin release of nanoparticles in varying glucose levels in vitro.
Figure 8B:
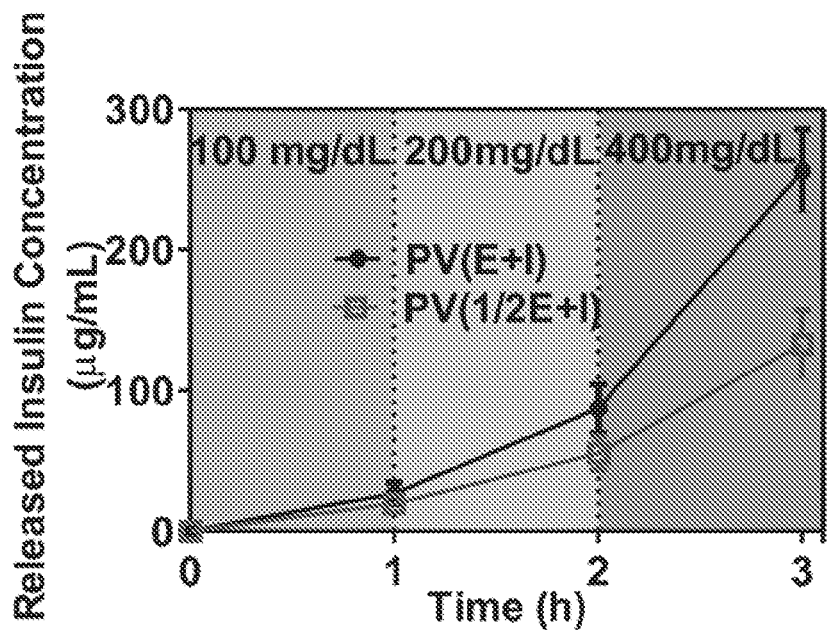
Figure 8C:
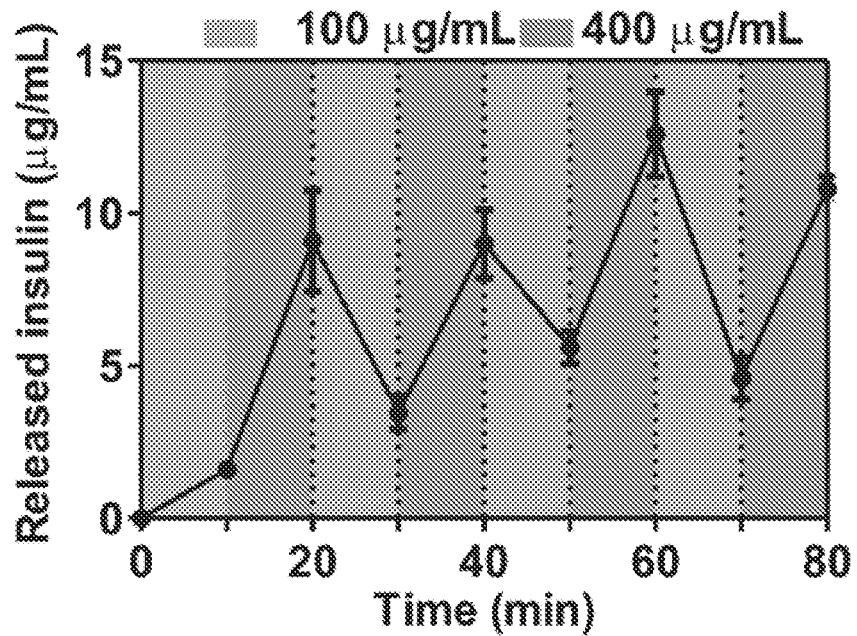
Figure 8D:
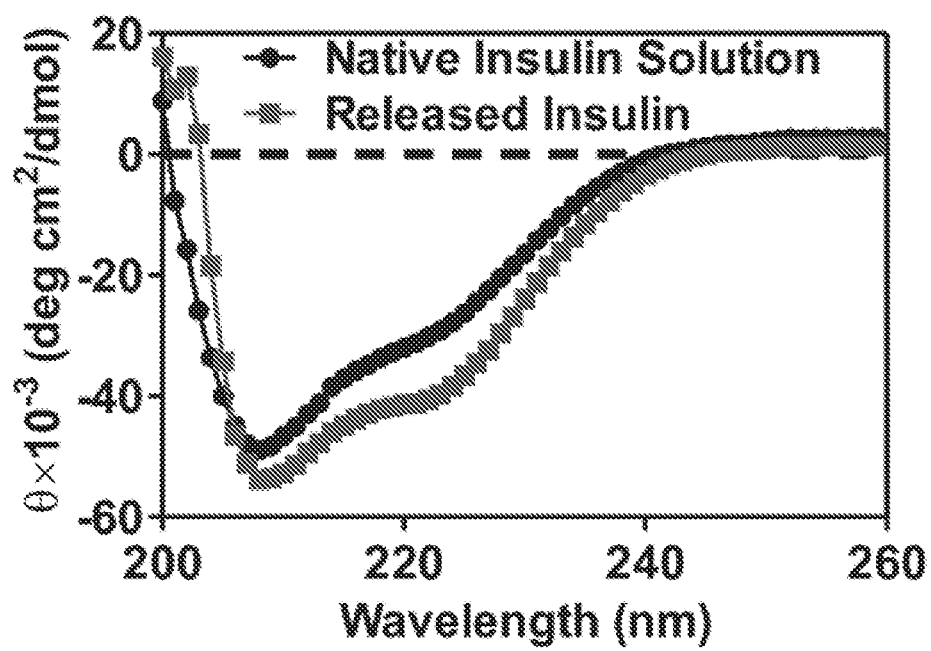

In vitro insulin release of nanoparticles was further assessed in response to different glucose levels by incubating nanoparticles with PBS containing various concentrations of glucose, including a control level (0 mg/dL), a normoglycemic level (100 mg/dL), and a hyperglycemic level (400 mg/dL). A significantly rapid insulin release rate was observed at the hyperglycemic glucose concentration, while limited insulin release was observed at the normoglycemic and control levels (FIG. 8A). This release profile was consistent with the above-mentioned dissociation response. When the glucose concentration was increased stepwise over time (100 mg/dL at time zero, 200 mg/dL at one hour, and 400 mg/dL at two hours), the release rate (slope) of insulin, increased correspondingly (FIG. 8B). These results show PVs response to increasing glucose concentrations by increasing insulin release. When the glucose concentration varied periodically between 100 and 400 mg/dL for 10 min each step, a pulsatile release pattern was observed (FIG. 8C). These results showed the PVs have a rapid response to changing glucose concentrations. Furthermore, when the GOx content in the PVs was reduced by one half (PV(1/2E+I)), the release rate of insulin decreased correspondingly (FIG. 8B). These results showed the insulin release rate could be adjusted by varying the GOx content in PVs. Notably, released insulin had identical secondary structure to that of native, non-encapsulated insulin (FIG. 8D), and is thus likely identical in function and activity as native insulin. Collectively, these results verified that the release of insulin from the PVs was in a glucose-responsive manner with fast and adaptable responsiveness.

Figure 9A:
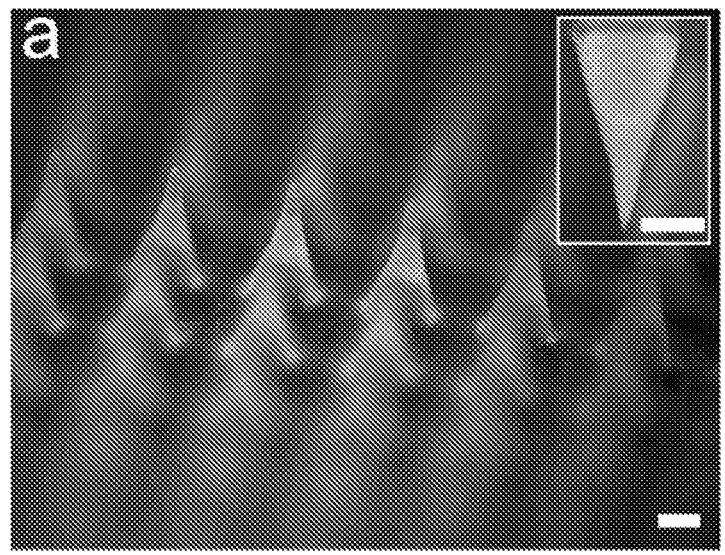
FIGS. 9A-C show hyaluronic acid (HA)-based microneedle (MN) array patch capable of administering PVs.
Figure 9B:
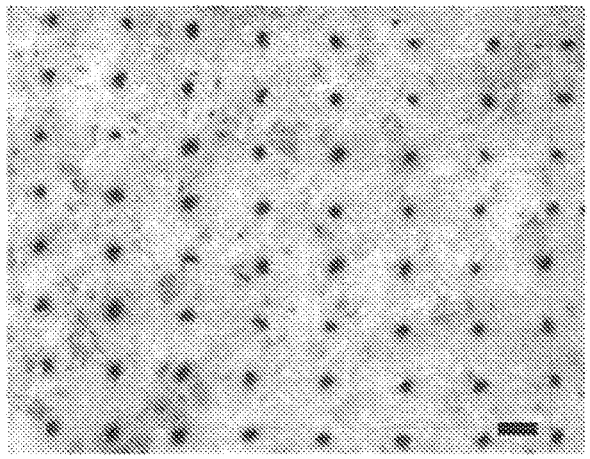
Figure 9C:
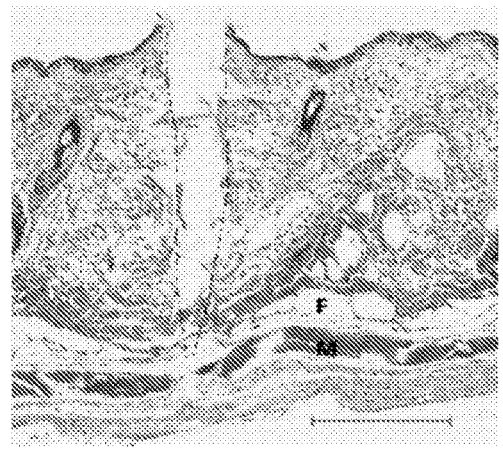

To achieve convenient and painless administration, insulin-loaded PVs were deposited in the tips of cross-linked hyaluronic acid (HA)-based microneedle (MN) array patch using a micromolding approach. See Yu, et al., *Proc. Natl. Acad. Sci.*, 2015, 112:8260. The resultant MN was arranged in a 20×20 array with 600 μm tip-to-tip spacing in a 100-mm² patch. Fluorescence imaging of MNs integrated with FITC-insulin-loaded PVs showed PVs were well distributed in the tip region of each needle (FIG. 9A). The MNs were administered on the back of the mice and penetrated mouse skin easily and conveniently, as shown by the trypan blue staining of mouse skin (FIG. 9B) and by hematoxylin and eosin stain (H&E) staining of resected mouse skin tissue (FIG. 9C). The mechanical strength of MN was about 3 N/needle in a tensile compression machine, which was sufficient to insert into skin without tip breakage. See Gittard, et al., *J. Adhes. Sci. Technol.*, 2013, 27:227.

Figure 10A:
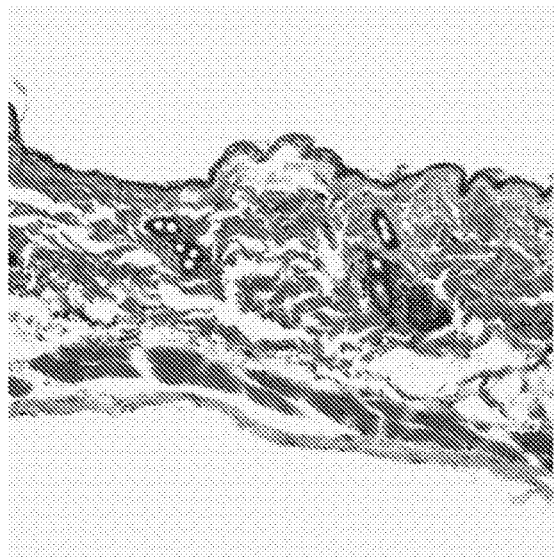
FIGS. 10A-E show biocompatibility of PVs and MN patches containing PVs. H&E-staining was performed on skin sections administered with a MN patch (FIG. 10A) and surrounding tissues (FIG. 10B) two days post-administration. (Scale bar: 100 μm). Photographs of skin puncture marks were taken at 5 min (FIG. 10C), 30 min (FIG. 10D), and 6 hours (FIG. 10E) post-treatment.
Figure 10B:
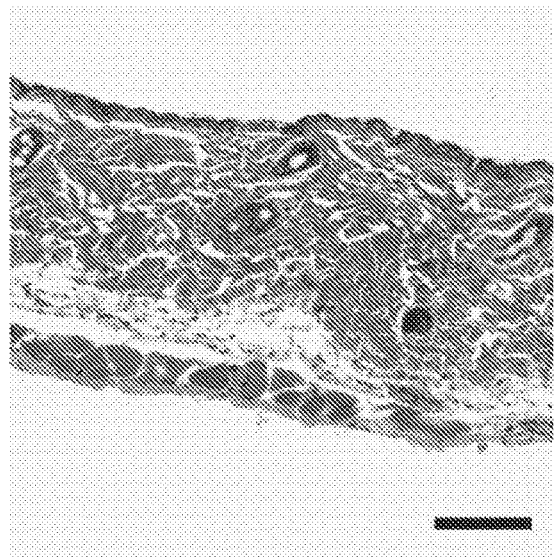
Figure 10C:
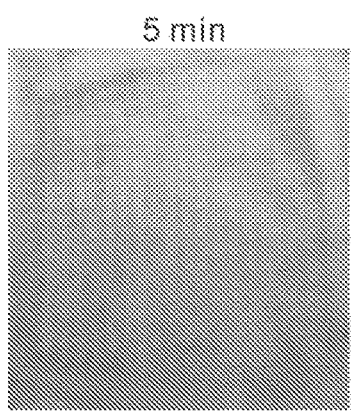
Figure 10D:
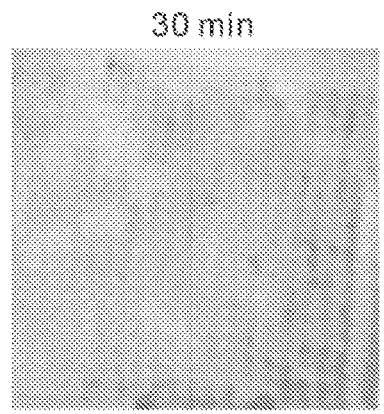

To evaluate the biocompatibility of the system, the cytotoxicity of PVs toward HeLa cells was investigated at different concentrations of PVs ranging from 0.1 to 1.0 mg/mL using a 3-(4,5)-dimethylthiahiazo(-z-yl)-3,5-di-phenytetrazoliumromide (MTT) assay. No significant toxicity of PVs was observed at any PV concentration studied. In vivo assessment of patch cytotoxicity also no significant inflammation in the region of patch two days post-administration (FIG. 10A) compared to surrounding tissue (FIG. 10B).

Figure 10E:
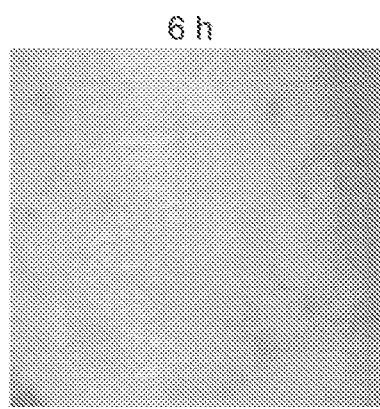

Further, the microchannel lesions on the skin created by insertion of the sharp MNs recovered within six hours post-administration (FIG. 10E). These results showed the PVs and the MN patch containing PVs have good biocompatibility.

The MN-array patch was administered on streptozotocin (STZ)-induced type 1 diabetic mice to evaluate the patch's in vivo performance for type 1 diabetes treatment. Mice were randomly divided into four groups and transcutaneously treated with different MN patch samples: 1) empty MNs containing only cross-linked HA (MN[HA]); 2) MNs loaded with insulin (MN[I]); 3) MNs loaded with PVs encapsulating only insulin (MN[PV(I)]); or 4) MNs loaded with PVs encapsulating GOx enzyme and insulin (MN[PV(E+I)]). The equivalent insulin dose was 10 mg/kg for each mouse. Blood/plasma glucose levels of treated mice in each group were monitored over time.

Figure 11A:
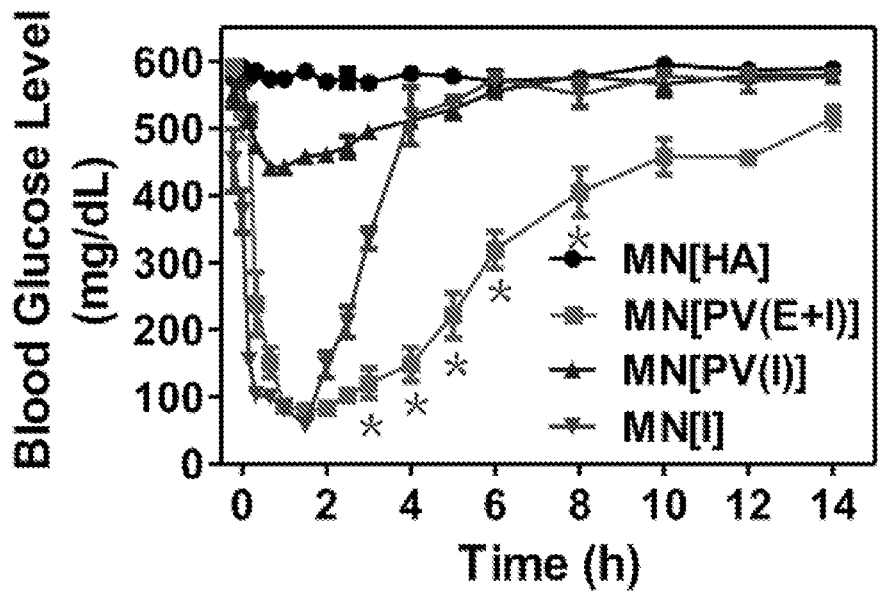
FIGS. 11A-B are graphs showing blood glucose concentrations in diabetic mice treated with MN[I] and MN[PV (E+I)].
Figure 11B:
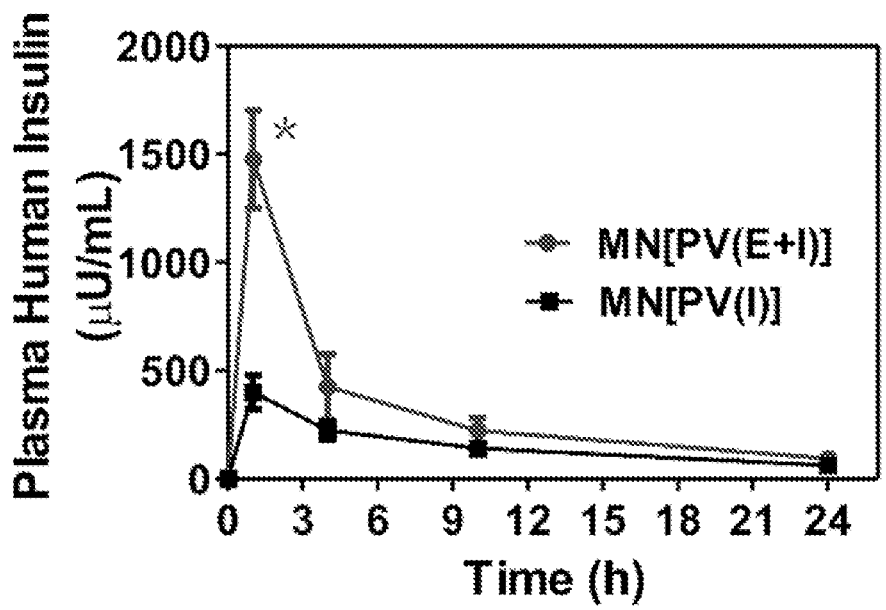

Blood glucose in mice treated with MN[I] and MN[PV(E+I)] rapidly decreased to about 90 mg/dL within 1 hour (FIG. 11A). However, the MN[I] group quickly lost control over glucose concentrations by the subsequent hour. To the contrary, the MN[PV(E+I)] group remained in the normoglycemic range (<200 mg/dL) for ~5 hours, with a subsequent gradual increase in blood glucose levels. The control and MN[PV(I)] group animals showed insignificant decreases in glucose, showing the requirement of GOx for adequate PV disassembly and insulin release. Insulin in plasma of treated mice was quantified by an enzyme-linked immunosorbent assay (ELISA). Mice treated with MN[PV(E+I)] had higher plasma insulin levels than mice administered with MN[PV(I)] for at least 24 hours (FIG. 11B), again showing the role of GOx in PV dissociation and insulin release.

Figure 12A:
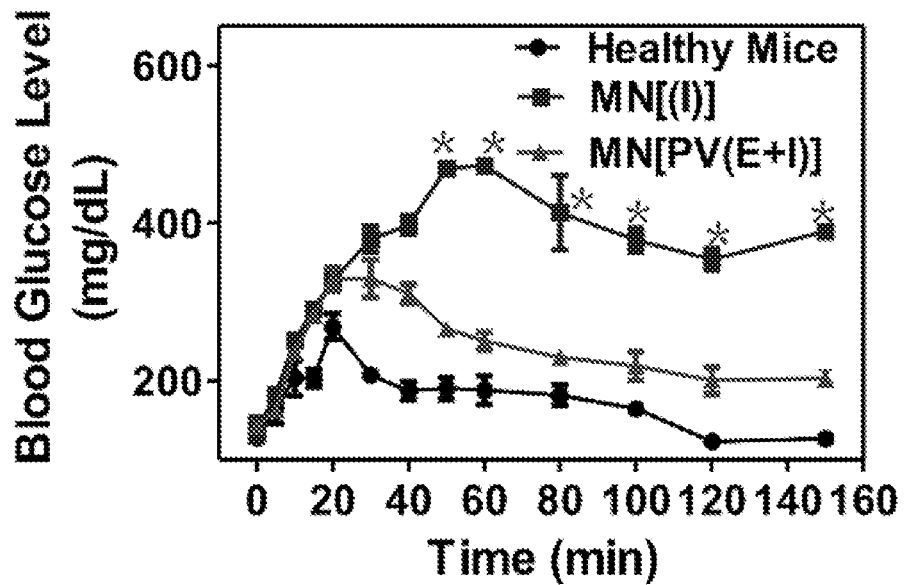
FIGS. 12A-B are graphs showing glucose tolerance of patch-treated mice.
Figure 12B:
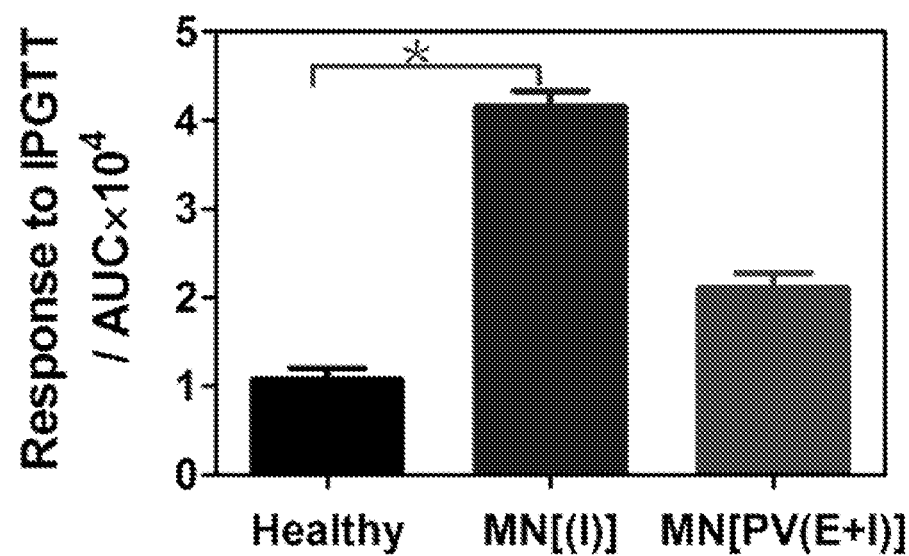

A glucose tolerance test of patch-treated mice was conducted via intraperitoneally (i.p.) injecting 1.5 g/kg glucose solution in diabetic mice one hour after administration of MN[PV(E+I)] or MN[I] patches. Healthy (non-diabetic) mice were also injected with glucose solution in the absence of MN patch administration. One hour after administering MN patches, the two groups of diabetic mice (MN[PV(E+I)] and MN[I]) had similar starting glucose levels as the untreated healthy mice. After i.p. injection of glucose, blood glucose levels of the three groups increased steadily, reaching their peaks (268, 330, and 470 mg/dL) at 20, 30, and 50 min for MN[PV(E+I)]-treated diabetic mice, MN[I]-treated diabetic mice, and untreated healthy mice, respectively (FIG. 12A). Thereafter, glucose levels declined gradually. After about 120 min, the MN[PV(E+I)] mice returned to normoglycemic range (<200 mg/dL), while MN[I] mice had glucose levels remaining at about 400 mg/dL. To quantify the glucose response to i.p. glucose injection, the area under the blood glucose level curve between 0 and 150 min in FIG. 12A was calculated for each group. The MN[PV(E+I)]-treated mice showed significantly improved resistance to glucose challenge compared to MN[I]-treated mice (FIG. 12B).

Figure 13A:
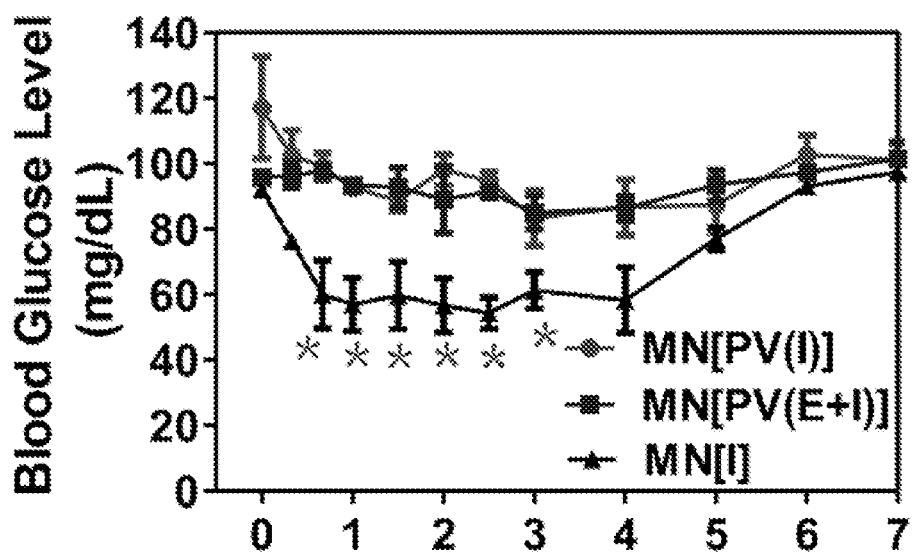
FIGS. 13A-B are graphs showing hypoglycemic potential of MN patches containing PVs.
Figure 13B:
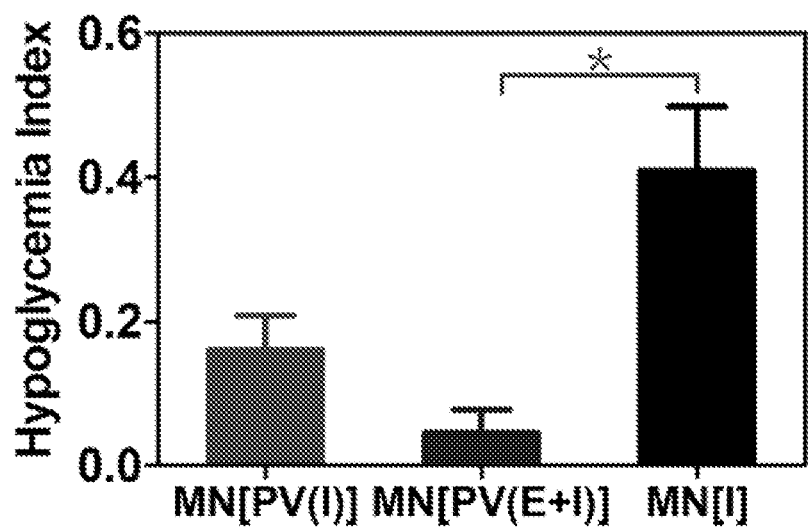

Commercially acceptable nanoparticles for diabetes treatment should demonstrate sufficient control over glucose levels, modulating glucose levels when needed and refraining therefrom when not needed. In view of the MN[PV(E+I)] patch's capabilities to significantly reduce blood glucose levels, it could be envisioned that the patch could also reduce glucose levels during hypoglycemic conditions. Therefore, to evaluate the hypoglycemic potential of the patches, MN[PV(E+I)], MN[PV(I)] and MN[I] were applied to healthy mice. Remarkable decreases in glucose were observed in mice treated with MN[I] (containing non-encapsulated insulin), while very little change occurred in mice treated with MN[PV(E+I)] or MN[PV(I)] (FIG. 13A). These results showed negligible insulin leakage occurred from MN[PV(E+I)] and MN[PV(I)], which reduced risk of hypoglycemia compared with MN[I]. To quantify these differences and evaluate the risk of hypoglycemia, the hypoglycemia index was calculated and graphed (FIG. 13B)). See Chou, et al., *Proc. Natl. Acad. Sci.*, 2015, 112:2401; Yu, et al., *Proc. Natl. Acad. Sci.*, 2015, 112:8260. PV-loaded MNs demonstrated a significantly lower hypoglycemic index compared to insulin-loaded MN.

Provided herein is a novel closed-loop, glucose-responsive insulin delivery platform which uses $H_2O_2$-responsive polymeric nanoparticles. The nanoparticles can be integrated with a painless transcutaneous MN array patch. Utilizing polymeric nanoparticles, water-soluble insulin was encapsulated into the inner cavity with a high capacity. This formulation demonstrated both in vitro and in vivo glucose-mediated disassembly, releasing the encapsulated insulin under the hyperglycemic condition with fast responsiveness. Importantly, when the glucose levels reached the normoglycemic state, the release rate of insulin declined, which avoids the risk of hypoglycemia. As such, the prepared insulin patch provides clinical closed-loop insulin delivery with a novel trigger mechanism to mimic the function of pancreatic beta-cells to release insulin in a glucose-responsive fashion. Furthermore, this $H_2O_2$-responsive artificial nanoparticle can be applied as a useful platform for delivering various therapeutics to treat other diseases. See Lu, et al., *Nat. Rev. Mater.*, 2016, 1:16075.

Materials and Methods

Chemicals. All chemicals were purchased from Sigma-Aldrich unless otherwise specified and were used as received. Sodium HA (molecular mass of 300 kDa) was purchased from Freda Biochem Co., Ltd. (Shandong, China). Human recombinant insulin (27.5 IU/mg of Zn salt) was purchased from Life Technology (U.S.A.). Poly(ethylene glycol) amine (PEG2000-NH2) was purchased from Laysan Bio, Inc. (U.S.A.). The deionized water was obtained by a Millipore NanoPure purification system (resistivity >18.2 MΩ.cm). All the organic solvents for synthesis and analysis were ordered from Fisher Scientific Inc. and used as received.

Synthesis and Characterizations of Acrylate Modified HA (m-HA). m-HA was synthesized according to the literature. See Wang, et al., *Nano Letters*, 2016, 16:2334. Briefly, 2.0 g of HA was dissolved in 100 mL of DI water at 4° C., to which 1.6 mL of methacrylic anhydride (MA) was added drop-wise. The reaction solution was adjusted to pH 8-9 by the addition of 5 N NaOH and stirred at 4° C. for 24 h. The resulting polymer was obtained by precipitation in acetone. The product was re-dissolved in DI water and the solution was dialyzed against DI water for 2 days. m-HA was obtained by lyophilization (Yield: 86%). The degree of modification was calculated to be 15% by comparing the ratio of the areas under the proton peaks at 5.74 and 6.17 ppm (methacrylate protons) to the peak at 1.99 ppm (N-acetyl glucosamine of HA). m-HA: 1H NMR ($D_2O$, 300 MHz, δ ppm): 1.85-1.96 (m, 3H, $CH_2$=C($CH_3$)CO), 1.99 (s, 3H, $NHCOCH_3$), 5.74 (s, 1H, $CH_1H_2$=C($CH_3$)CO), 6.17 (s, 1H, $CH_1H_2$=C($CH_3$)CO).

Synthesis of Boronic Esters Functionalized Block Copolymer. 4-(Imidazoyl carbamate)phenylboronic acid pinacol ester (1) was prepared according to the literature. Broaders, et al., *J. Am. Chem. Soc.*, 2010, 133:756. Briefly, 4-(Hydroxymethyl)phenylboronic acid pinacol ester (PAPE) (4g, 17.1 mmol) was dissolved in dry dichloromethane ($CH_2Cl_2$)

(20 mL) in a dried 200-mL flask. Carbonyldiimidazole (CDI) (5.54 g, 34.2 mmol) was then added to the solution and stirred for 1 h. The mixture was concentrated under vacuum, redissolved in ethyl acetate (200 mL) and washed with $H_2O$ (3×10 mL). The organics were dried with $MgSO_4$, and concentrated using rotary evaporator to give a pure white solid 1 (3.90 g, yield: 70.0%). 1: $^1$HNMR (400 MHz, $CDCl_3$) δ 1.33 (s, 12 H), 5.42 (s, 2 H), 7.05 (s, 1H), 7.43 (m, 3H), 7.85 (d, 2H), 8.14 (s, 1H).

mPEG$_{44}$-b-polyserine$_{60}$ (1.0 g, 7.5 mmol OH) was first synthesized according to the literature. See Tai, et al., *Biomacromolecules*, 2014, 15:3495. The polymer was then dissolved in anhydrous $CH_2Cl_2$ (20 mL) in a 50 mL of flask. 4-(Imidazoyl carbamate)phenylboronic acid pinacol ester (2.5 g, 7.5 mmol) was added followed by DMAP (0.9 g, 7.5 mmol) addition, and the mixture solution was stirred overnight at room temperature. The product mPEG-b-P(Ser-PBE) was obtained by precipitation in cold diethyl ether and dried in vacuo.

By this method, 4-(hydroxymethyl)phenylboronic acid pinacol ester is activated by CDI to an active form, 4-(imidazoyl carbamate)phenylboronic acid pinacol ester. After conjugation with serine, the polymer then becomes a 4-(hydroxymethyl)phenylboronic acid pinacol ester (PBE) conjugated polymer.

Preparation of Polymeric Nanoparticles. Polymeric nanoparticles (PVs) were prepared by the solvent evaporation method. Briefly, 40 mg of mPEG-b-P(Ser-PBE) was dissolved in 5 mL of THF, followed by injection of 10 mL of DI water with or without 7.5 mg of human insulin and 0.75 mg of GOx dissolved in it. The mixture was stirred at room temperature for 30 min, and then THF was removed by bubbling with $N_2$. The unloaded insulin was removed by centrifugation at 4000×g for 10 min with a centrifugal filter (25,000 Da molecular mass cutoff, Millipore) and washed with PBS buffer for several times. The obtained PVs suspension was stored at 4° C. for further studies. The loading content and loading efficiency of insulin was tested using a Coomassie Plus protein assay. The absorbance was detected at 595 nm on the Infinite 200 PRO multimode plate reader (Tecan Group Ltd., Switzerland) and the concentration was interpolated from an insulin standard curve. The size distribution and zeta-potential of the PVs were measured using the Zeta sizer (Nano ZS; Malvern). The TEM images were acquired using a JEOL 2000FX TEM.

Mechanical Strength Test. The mechanical strength of MNs was tested by pressing arrays of MNs against a stainless-steel plate on an MTS 30G tensile testing machine. The initial gauge was set at 2.00 mm between the MN tips and the stainless-steel plate, with 10.00 N as the load cell capacity. The speed of the top stainless-steel plate movement towards the MN-array patch was 0.1 mm/s. The failure force of MNs was recorded as the needle began to buckle.

In Vitro Insulin Release Studies. 8 mg of polymeric nanoparticles were added to PBS (1 mL) with different glucose concentrations (0, 100, or 400 mg/dL) and incubated at 37° C. on an orbital shaker to evaluate the release of insulin. At predetermined time points, 50 μL of the sample was taken out for analysis and 50 μL of fresh media was then added to the well to maintain a constant volume and placed back to the incubator. Insulin content in the withdrawn sample was determined by absorbance measurement at 595 nm and by virtue of the insulin standard curve. To access the responsiveness of PVs to changes in glucose levels, PVs were first incubated in 100 mg/dL glucose solution for 10 min, then were separated by a centrifugal filter (100,000 Da molecular mass cutoff, Millipore), and then incubated in 400 mg/dL glucose for another 10 min. This cycle was repeated several times and the released insulin was measured.

The $H_2O_2$-responsive capability of nanoparticles were tested by adding 8 mg of polymeric nanoparticles to PBS (1 mL) with different $H_2O_2$ concentrations (0, 50, 200 μm) and incubated at 37° C. on an orbital shaker to evaluate the release of insulin. The released insulin was tested as the above method.

Biocompatibility Analysis. The in vitro cytotoxicity of PVs was tested using MTT assay towards HeLa cells. Briefly, HeLa cells were seeded in 96-well plate at a density of 6000 cells per well. After 24 h incubation in 200 μL of Dulbecco's Modified Eagle Medium (DMEM) with 10% fetal bovine growth serum (FBS), series dilutions of PVs ranging from 0.1 to 1 mg/mL were added into wells. After 24 h incubation, thiazolyl blue solution (5 mg/mL) was added into wells and incubated with cells for another 4 h. After removing the culture media, the purple formazan crystal was dissolved in 150 μL of DMSO. The absorbance of the plates at 570 nm, which is directly proportional to the viable cell number, was measured on multimode plate reader.

The in vivo biocompatibility of MN patch was evaluated using histological analysis. Briefly, blank HA MN (hyaluronic acid-formed MN without PV, E, or I), MN[PV(E+I)], and MN[I] were transcutaneously pierced into the back of the mice for 10 h. After 24 h, the mice were euthanized by $CO_2$ asphyxiation and the surrounding tissues were excised. The tissues were fixed in 10% formalin, and then embedded in paraffin, cut into 5 μm sections, and stained using hematoxylin and eosin (H&E) and fluorescent TUNEL staining for histological analysis.

In Vivo Studies Using STZ-Induced Diabetic Mice. The in vivo performance of the prepared MN-array patches was assessed on STZ-induced adult diabetic mice (male C57B6, 20-25 g, Jackson Lab) for diabetes management. The animal study protocol was approved by the Institutional Animal Care and Use Committee at North Carolina State University and University of North Carolina at Chapel Hill. The mice were divided into four groups randomly with five mice for each group and transcutaneously treated with empty MN containing only m-HA, MN loaded with insulin MN[I], MN loaded with PVs encapsulating insulin and enzyme MN[PV (E+I)], or MN loaded with PVs encapsulating only insulin MN[PV(I)], respectively. The insulin dose was 10 mg/kg for each mouse. The plasma glucose levels of the mice in each group were monitored over time (at 10, 20, 40, and 60 min, and once per hour afterwards) by collecting blood samples (~3 μL) from the tail vein and determined using the Clarity GL2Plus glucose meter (Clarity Diagnostics, Boca Raton, Fla.) until a return to stable hyperglycemia. To measure the plasma insulin concentration in vivo, blood samples (25 μL) were collected from the tail vein. The serum was isolated and stored at −20° C. for plasma insulin assay using Human Insulin ELISA kit according to the manufacturer's protocol (Calbiotech, U.S.A.). An intraperitoneal glucose tolerance test (IPGTT) was conducted to verify the in vivo glucose responsiveness of MNs 1 h post administration of MNs. Briefly, mice were administrated with MN[PV(E+I)] and MN[I] (the insulin dose was 10 mg/kg for each mouse), and then a glucose solution in PBS buffer was intraperitoneally injected with glucose dose of 1.5 g/kg for each mouse and the blood glucose levels were monitored over time. The side effects of MNs were evaluated on healthy mice by administration with MN[PV(E+I)], MN[PV(I)] and MN[I].

Statistics. All data presented are Mean±s. d. Statistical analysis was performed using Student's t-test. The differences between experimental groups and control groups were considered statistically significant for P value <0.05.

Publications cited herein are hereby specifically incorporated by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention That which is claimed is:

1. A nanoparticle comprising:
    a copolymer comprising a polyethylene glycol polymer, a polyhydroxylated polymer, and a peroxide-sensitive pendant group;
    a glucose-responsive agent; and
    a therapeutic agent;
    wherein the peroxide-sensitive pendant group comprises a boronic ester; and
    wherein the copolymer encapsulates the glucose-responsive agent and the therapeutic agent.

2. The nanoparticle of claim 1, wherein the polyhydroxylated polymer comprises a polyamino acid.

3. The nanoparticle of claim 1, wherein the polyhydroxylated polymer comprises polyserine.

4. The nanoparticle of claim 1, wherein the peroxide-sensitive pendant group is attached to the copolymer by a carbonate bond.

5. The nanoparticle of claim 1, wherein the peroxide-sensitive pendant group detaches from the copolymer upon exposure to peroxide.

6. The nanoparticle of claim 1, wherein detachment of the peroxide-sensitive pendant group facilitates disassembly of the nanoparticle.

7. The nanoparticle of claim 1, wherein the glucose-responsive agent comprises glucose oxidase.

8. The nanoparticle of claim 1, wherein the therapeutic agent comprises insulin.

9. A medicament comprising the nanoparticle of claim 1 and a pharmaceutically acceptable excipient.

10. A device comprising:
    a plurality of microneedles each having a base end and a tip;
    a substrate to which the base ends of the microneedles are attached; and
    a plurality of nanoparticles of claim 1.

11. A method of delivering a therapeutic agent to a subject in need thereof, the method comprising:
    (a) administering to the subject, a nanoparticle comprising:
        (i) a copolymer comprising a polyethylene glycol polymer, a polyhydroxylated polymer, and a peroxide-sensitive pendant group;
        (ii) a glucose-responsive agent; and
        (iii) a therapeutic agent;
        wherein the peroxide-sensitive pendant group comprises a boronic ester; and
        wherein the copolymer encapsulates the glucose-responsive agent and the therapeutic agent; and
    (b) releasing the therapeutic agent from the nanoparticle in the presence of hyperglycemic levels of glucose.

12. The method of claim 11, wherein the subject has hyperglycemia.

13. The method of claim 11, wherein the glucose-responsive agent metabolizes glucose to produce a peroxide.

14. The method of claim 13, further comprising detaching the peroxide-sensitive pendant group from the copolymer upon exposure to the peroxide.

15. The method of claim 14, wherein the detaching step facilitates disassembly of the nanoparticle, thereby releasing the therapeutic agent from the nanoparticle.

16. The method of claim 11, wherein the therapeutic agent comprises insulin.

17. The method of claim 11, wherein the method further comprises reducing blood glucose levels.

18. The method of claim 17, wherein blood glucose levels are reduced to no lower than normoglycemic levels.

* * * * *